United States Patent
Hamada et al.

(10) Patent No.: US 7,799,941 B2
(45) Date of Patent: Sep. 21, 2010

(54) PROCESS FOR PRODUCING OPTICALLY ACTIVE β-HYDROXY-α-AMINOCARBOXYLIC ACID DERIVATIVE

(75) Inventors: Yasumasa Hamada, Chiba (JP); Kazuishi Makino, Chiba (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 1268 days.

(21) Appl. No.: 10/563,763

(22) PCT Filed: Jul. 9, 2004

(86) PCT No.: PCT/JP2004/009829

§ 371 (c)(1), (2), (4) Date: Jan. 9, 2006

(87) PCT Pub. No.: WO2005/005371

PCT Pub. Date: Jan. 20, 2005

(65) Prior Publication Data

US 2006/0167300 A1    Jul. 27, 2006

(30) Foreign Application Priority Data

Jul. 10, 2003 (JP) .............................. 2003-272637
Dec. 24, 2003 (JP) .............................. 2003-426226

(51) Int. Cl.
*C07C 229/08* (2006.01)
(52) U.S. Cl. .................... 560/42; 560/170; 562/564
(58) Field of Classification Search .................. 560/42, 560/170; 562/564
See application file for complete search history.

(56) References Cited

U.S. PATENT DOCUMENTS

| 4,933,482 A | 6/1990 | Sayo et al. | |
| 2008/0139825 A1 * | 6/2008 | Hamada et al. | 549/65 |

FOREIGN PATENT DOCUMENTS

| JP | A 02-172956 | 7/1990 |
| JP | A 06-080617 | 3/1994 |
| JP | A 63-310847 | 12/1998 |

OTHER PUBLICATIONS

Labeeuw et al., Assymetry; Tetrahedron, 15; pp. 1899-1908, (2004).*

Noyori et al., "Stereoselective Hydrogenation via Dynamic Kinetic Resolution," J. Am. Chem. Soc., vol. 111 , pp. 9134-9135 (1989).
Schmidt et al., "Total Synthesis of the Biphenomycins; V.[1] Synthesis of Biphenomycin A[2]," Synthesis, pp. 1248-1254 (1992).
Noyori, "Assymetric Catalysis in Organic Synthesis," John Wiley & Sons, Inc., New York (1994) pp. 1-17.
Noyori, "Assymetric Catalysis in Organic Synthesis," John Wiley & Sons, Inc., New York (1994) pp. 56-95.

* cited by examiner

*Primary Examiner*—James O Wilson
*Assistant Examiner*—Ebenezer Sackey
(74) *Attorney, Agent, or Firm*—Oliff & Berridge, PLC

(57) ABSTRACT

There is provided a process for efficiently producing an anti form of an optically active β-hydroxy-α-aminocarboxylic acid derivative that is useful as an intermediate for pharmaceuticals and agrochemicals. The process for producing optically active β-hydroxy-α-aminocarboxylic acid derivative of formula (2) or (3)

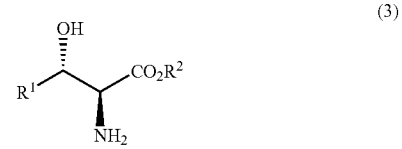

wherein $R^1$ is substituted or unsubstituted $C_{1-20}$ alkyl group, or substituted or unsubstituted $C_{4-12}$ aromatic group, $R^2$ is substituted or unsubstituted $C_{1-20}$ alkyl group, or substituted or unsubstituted $C_{4-12}$ aromatic group, characterized by comprising subjecting an α-aminoacyl acetic acid ester compound of formula (1)

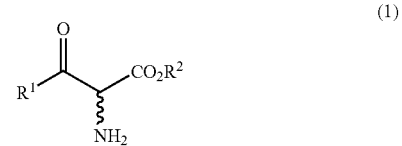

wherein $R^1$ and $R^2$ have the same meaning as the above, to hydrogenation by catalytic asymmetric hydrogenation in the presence of an acid.

12 Claims, No Drawings

PROCESS FOR PRODUCING OPTICALLY ACTIVE β-HYDROXY-α-AMINOCARBOXYLIC ACID DERIVATIVE

TECHNICAL FIELD

The present invention relates to a process for producing optically active β-hydroxy-α-aminocarboxylic acid derivative that is useful as an intermediate for pharmaceuticals and agrochemicals.

BACKGROUND ART

Optically active β-hydroxy-α-aminocarboxylic acid derivatives are important intermediates for compounds useful as several fine chemical materials represented by physiologically active substances such as pharmaceuticals and agrochemicals, etc.

As a process for producing optically active β-hydroxy-α-aminocarboxylic acid derivative, a process is known in which a racemic α-aminoacyl acetic acid ester compound is subjected to asymmetric hydrogenation by catalytic asymmetric hydrogenation with ruthenium-optically active phosphine complex catalyst to produce syn-selectively an optically active β-hydroxy-α-aminocarboxylic acid derivative (see, for example, Non-patent Documents 1 and 2, and Patent Document 1).

In addition, asymmetric hydrogenation with a transition metal catalyst of olefins, ketones and imines has been known well (see, for example, Non-patent Document 3).

Patent Document 1: JP-A-6-80617 (1994)
Non-patent Document 1: J. Am. Chem. Soc., 1989, 111, p. 9134-9135
Non-patent Document 2: SYNTHESIS, 1992, p. 1248-1254
Non-patent Document 3: R. Noyori ed. Asymmetric Catalysis in Organic Synthesis, (1994) Jhon Wiley &; Sons, Inc, New York

DISCLOSURE OF INVENTION

Problem to be Solved by the Invention

The processes disclosed in Non-patent Documents 1 and 2 and Patent Document 1 are excellent as processes for selectively producing the syn form of optically active β-hydroxy-α-aminocarboxylic acid derivative.

However, as these processes cannot directly produce the anti form of optically active β-hydroxy-α-aminocarboxylic acid derivative, it was required to produce the syn form once and revert the configuration of the one side in order to produce the anti form.

Therefore, the process for directly producing the anti form of optically active β-hydroxy-α-aminocarboxylic acid derivative has been desired.

Means for Solving the Problem

The present inventors eagerly investigated as to processes for directly producing the anti form of optically active β-hydroxy-α-aminocarboxylic acid derivative. As a result of it, they found that the anti form of optically active β-hydroxy-α-aminocarboxylic acid derivative can be easily obtained in a selective manner by subjecting an α-aminoacyl acetic acid ester compound that the amino group is unsubstituted to hydrogenation by catalytic asymmetric hydrogenation in the presence of an acid, and they completed the present invention.

That is, the present invention pertains to the followings:

1. A process for producing optically active β-hydroxy-α-aminocarboxylic acid derivative of formula (2) or (3)

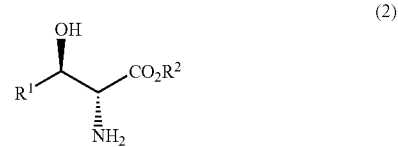

(2)

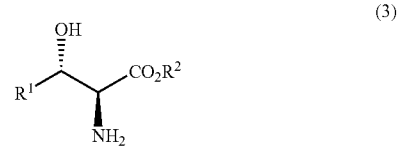

(3)

wherein $R^1$ is $C_{1-20}$ alkyl group [the $C_{1-20}$ alkyl group may be arbitrarily substituted with $C_{4-12}$ aromatic group (the aromatic group may be arbitrarily substituted with halogen atom, $C_{1-6}$ alkyl group, $C_{1-6}$ alkoxy group, $C_{1-6}$ alkoxycarbonyl group, $C_{1-6}$ alkylcarbonyloxy group or $CONR^4R^5$ wherein $R^4$ and $R^5$ are independently of each other are hydrogen atom or $C_{1-6}$ alkyl group), $C_{1-6}$ alkoxy group, $C_{1-6}$ alkoxycarbonyl group or $CONR^4R^5$ wherein $R^4$ and $R^5$ are independently of each other are hydrogen atom or $C_{1-6}$ alkyl group], or $C_{4-12}$ aromatic group [the aromatic group may be arbitrarily substituted with halogen atom, $C_{1-6}$ alkyl group, $C_{1-6}$ alkoxy group, $C_{1-6}$ alkoxycarbonyl group, $C_{1-6}$ alkylcarbonyloxy group (the $C_{1-6}$ alkyl group, $C_{1-6}$ alkoxy group, $C_{1-6}$ alkoxycarbonyl group and $C_{1-6}$ alkylcarbonyloxy group may be arbitrarily substituted with $C_{4-12}$ aromatic group (the aromatic group may be arbitrarily substituted with halogen atom)) or $CONR^4R^5$ wherein $R^4$ and $R^5$ are independently of each other are hydrogen atom or $C_{1-6}$ alkyl group], $R^2$ is $C_{1-20}$ alkyl group [the $C_{1-20}$ alkyl group may be arbitrarily substituted with $C_{4-12}$ aromatic group (the aromatic group may be arbitrarily substituted with halogen atom, $C_{1-6}$ alkyl group, $C_{1-6}$ alkoxy group, $C_{1-6}$ alkoxycarbonyl group, $C_{1-6}$ alkylcarbonyloxy group or $CONR^4R^5$ wherein $R^4$ and $R^5$ are independently of each other are hydrogen atom or $C_{1-6}$ alkyl group), $C_{1-6}$ alkoxy group, $C_{1-6}$ alkoxycarbonyl group or $CONR^4R^5$ wherein $R^4$ and $R^5$ are independently of each other are hydrogen atom or $C_{1-6}$ alkyl group], or $C_{4-12}$ aromatic group [the aromatic group may be arbitrarily substituted with halogen atom, $C_{1-6}$ alkyl group, $C_{1-6}$ alkoxy group, $C_{1-6}$ alkoxycarbonyl group, $C_{1-6}$ alkylcarbonyloxy group. or $CONR^4R^5$ wherein $R^4$ and $R^5$ are independently of each other are hydrogen atom or $C_{1-6}$ alkyl group], characterized by comprising subjecting an α-aminoacyl acetic acid ester compound of formula (1)

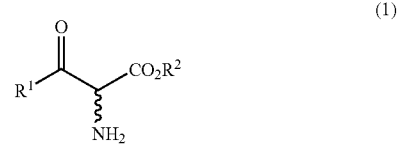

(1)

wherein $R^1$ and $R^2$ have the same meaning as the above, to hydrogenation by catalytic asymmetric hydrogenation in the presence of an acid;

2. The process for producing optically active β-hydroxy-α-aminocarboxylic acid derivative as set forth in 1., wherein the catalyst used for the catalytic asymmetric hydrogenation is a complex of a Group VIII transition metal of the Periodic Table having an optically active phosphine ligand;

3. The process for producing optically active β-hydroxy-α-aminocarboxylic acid derivative as set forth in 2., wherein the Group VIII transition metal of the Periodic Table is ruthenium, iridium or rhodium, and the optically active phosphine ligand is an optically active bidentate phosphine ligand;

4. The process for producing optically active β-hydroxy-α-aminocarboxylic acid derivative as set forth in 3., wherein the Group VIII transition metal of the Periodic Table is ruthenium, and the optically active bidentate phosphine ligand is represented by formula (4)

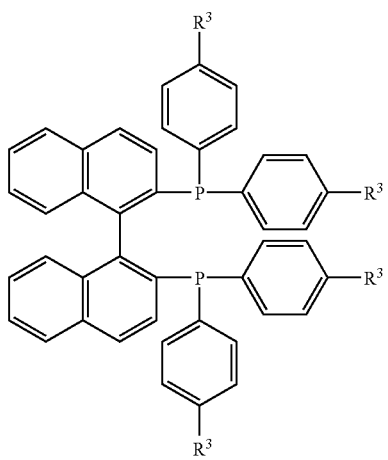

(4)

wherein $R^3$ is hydrogen atom, methyl group, or tertiary butyl group, absolute configuration is either S or R;

5. The process for producing optically active β-hydroxy-α-aminocarboxylic acid derivative as set forth in 4., wherein the complex of a Group VIII transition metal of the Periodic Table is $RuHX^1(R^3\text{-BINAP})_2$, $RuX^2{}_2(R^3\text{-BINAP})$ or $Ru_2Cl_4(R^3\text{-BINAP})_2(Et_3N)$ wherein $R^3$-BINAP is the optically active bidentate phosphine ligand of formula (4), Et is ethyl group, $X^1$ and $X^2$ independently of each other are Cl, $ClO_4$, $BF_4$, $PF_6$, $OCOCH_3$, $OCOCF_3$, OCO-t-Bu or $OSO_2CF_3$, the complex may be further coordinated with N,N-dimethylformamide, benzene, $AlCl_3$, $SnCl_4$, $TiCl_4$ or $ZnCl_2$;

6. The process for producing optically active β-hydroxy-α-aminocarboxylic acid derivative as set forth in 5., wherein the complex of a Group VIII transition metal of the Periodic Table is $RuX^2{}_2(R^3\text{-BINAP})$ wherein $X^2$ and $R^3$-BINAP have the same meaning as the above, the complex may be further coordinated with N,N-dimethylformamide, benzene, $AlCl_3$, $SnCl_4$, $TiCl_4$ or $ZnCl_2$;

7. The process for producing optically active β-hydroxy-α-aminocarboxylic acid derivative as set forth in 6., wherein $RuX^2{}_2(R^3\text{-BINAP})$ further coordinated with N,N-dimethylformamide or benzene wherein $X^2$ is Cl, $R^3$-BINAP has the same meaning as the above is used;

8. The process for producing optically active β-hydroxy-α-aminocarboxylic acid derivative as set forth in 3., wherein the Group VIII transition metal of the Periodic Table is iridium, and the optically active bidentate phosphine ligand is $R^3$-BINAP wherein $R^3$-BINAP has the same meaning as the above or a compound of formula (5)

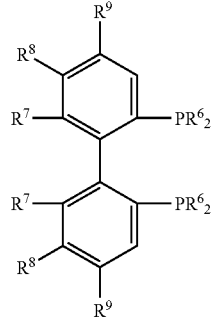

(5)

wherein $R^6$ is phenyl group, naphthyl group (the phenyl group and naphthyl group may be arbitrarily substituted with $C_{1-6}$ alkyl group or $C_{1-6}$ alkoxy group), cyclopentyl group or cyclohexyl group, $R^7$ is methyl group or methoxy group, $R^8$ is hydrogen atom, methyl group, methoxy group or chlorine atom, $R^9$ is hydrogen atom, methyl group, methoxy group, dimethylamino group or diethylamino group, absolute configuration is either S or R;

9. The process for producing optically active β-hydroxy-α-aminocarboxylic acid derivative as set forth in 8., wherein an acetic acid salt is added in the reaction system;

10. The process for producing optically active β-hydroxy-α-aminocarboxylic acid derivative as set forth in 9., wherein when the complex of a Group VIII transition metal of the Periodic Table is prepared, an iodine compound is added;

11. The process for producing optically active β-hydroxy-α-aminocarboxylic acid derivative as set forth in 10., wherein the optically active bidentate phosphine ligand is a compound of the formula (5);

12. The process for producing optically active β-hydroxy-α-aminocarboxylic acid derivative as set forth in 11., wherein when the complex of a Group VIII transition metal of the Periodic Table is prepared, $[Ir(cod)Cl]_2$ wherein cod is 1,5-cyclooctadiene is used;

13. The process for producing optically active β-hydroxy-α-aminocarboxylic acid derivative as set forth in any one of 1. to 12., wherein the acid is a strong acid.

Hereinafter, the present invention is described in further detail.

In the meantime, "n" means normal, "i" means iso, "s" means secondary, "t" means tertiary, "c" means cyclo, "o" means ortho, "m" means meta, "p" means para, "Me" means methyl group, "Et" means ethyl group, "Pr" means propyl group, "Bu" means butyl group, "Pen" means pentyl group, "Hex" means hexyl group, "Hep" means heptyl group, "Ph" means phenyl group, "Bn" means benzyl group, "Bz" means benzoyl group, "Ac" means acetyl group, "Ts" means para-toluenesulfonyl group and "Boc" means tertiary butoxy carbonyl group in this specification.

First of all, each substituent of substituents $R^1$ and $R^2$ is described.

Halogen atom includes fluorine atom, chlorine atom, bromine atom and iodine atom.

$C_{1-6}$alkyl group may be a straight-chain alkyl group or branched alkyl group, or contain $C_{3-6}$ cycloalkyl group, and includes for example methyl group, ethyl group, n-propyl group, i-propyl group, c-propyl group, n-butyl group, i-butyl group, s-butyl group, t-butyl group, c-butyl group, 1-methyl-c-propyl group, 2-methyl-c-propyl group, n-pentyl group, 1-methyl-n-butyl group, 2-methyl-n-butyl group, 3-methyl-n-butyl group, 1,1-dimethyl-n-propyl group, 1,2-dimethyl-n-propyl group, 2,2-dimethyl-n-propyl group, 1-ethyl-n-propyl group, c-pentyl group, 1-methyl-c-butyl group, 2-methyl-c-butyl group, 3-methyl-c-butyl group, 1,2-dimethyl-c-propyl group, 2,3-dimethyl-c-propyl group, 1-ethyl-c-propyl group, 2-ethyl-c-propyl group, n-hexyl group, 1-methyl-n-pentyl group, 2-methyl-n-pentyl group, 3-methyl-n-pentyl group, 4-methyl-n-pentyl group, 1,1-dimethyl-n-butyl group, 1,2-dimethyl-n-butyl group, 1,3-dimethyl-n-butyl group, 2,2-dimethyl-n-butyl group, 2,3-dimethyl-n-butyl group, 3,3-dimethyl-n-butyl group, 1-ethyl-n-butyl group, 2-ethyl-n-butyl group, 1,1,2-trimethyl-n-propyl group, 1,2,2-trimethyl-n-propyl group, 1-ethyl-1-methyl-n-propyl group, 1-ethyl-2-methyl-n-propyl group, c-hexyl group, 1-methyl-c-pentyl group, 2-methyl-c-pentyl group, 3-methyl-c-pentyl group, 1-ethyl-c-butyl group, 2-ethyl-c-butyl group, 3-ethyl-c-butyl group, 1,2-dimethyl-c-butyl group, 1,3-dimethyl-c-butyl group, 2,2-dimethyl-c-butyl group, 2,3-dimethyl-c-butyl group, 2,4-dimethyl-c-butyl group, 3,3-dimethyl-c-butyl group, 1-n-propyl-c-propyl group, 2-n-propyl-c-propyl group, 1-i-propyl-c-propyl group, 2-i-propyl-c-propyl group, 1,2,2-trimethyl-c-propyl group, 1,2,3-trimethyl-c-propyl group, 2,2,3-trimethyl-c-propyl group, 1-ethyl-2-methyl-c-propyl group, 2-ethyl-1-methyl-c-propyl group, 2-ethyl-2-methyl-c-propyl group and 2-ethyl-3-methyl-c-propyl group, etc.

$C_{1-20}$alkyl group may be a straight-chain alkyl group or branched alkyl group, or contain $C_{3-20}$ cycloalkyl group, and includes in addition to the above-mentioned substituents, 1-methyl-1-ethyl-n-pentyl group, n-heptyl group, 2-heptyl group, c-heptyl group, 1-ethyl-1,2-dimethyl-n-propyl group, 1-ethyl-2,2-dimethyl-n-propyl group, 1-octyl group, 3-octyl group, c-octyl group, 4-methyl-3-n-heptyl group, 6-methyl-2-n-heptyl group, 2-propyl-1-n-heptyl group, 2,4,4-trimethyl-1-n-pentyl group, 1-nonyl group, 2-nonyl group, 2,6-dimethyl-4-n-heptyl group, 3-ethyl-2,2-dimethyl-3-n-pentyl group, 3,5,5-trimethyl-1-n-hexyl group, 1-decyl group, 2-decyl group, 4-decyl group, 3,7-dimethyl-1-n-octyl group, 3,7-dimethyl-3-n-octyl group, n-undecyl group, n-dodecyl group, n-tridecyl group, n-tetradecyl group, n-pentadecyl group, n-hexadecyl group, n-heptadecyl group, n-octadecyl group, n-nonadecyl group and n-eicosyl, etc.

$C_{1-6}$ alkoxy group may be a straight-chain alkoxy group or branched alkoxy group, or contain $C_{3-6}$ cycloalkoxy group, and includes methoxy group, ethoxy group, n-propoxy group, i-propoxy group, c-propoxy group, n-butoxy group, i-butoxy group, s-butoxy group, t-butoxy group, c-butoxy group, 1-methyl-c-propoxy group, 2-methyl-c-propoxy group, n-pentyloxy group, 1-methyl-n-butoxy group, 2-methyl-n-butoxy group, 3-methyl-n-butoxy group, 1,1-dimethyl-n-propoxy group, 1,2-dimethyl-n-propoxy group, 2,2-dimethyl-n-propoxy group, 1-ethyl-n-propoxy group, c-pentyloxy group, 1-methyl-c-butoxy group, 2-methyl-c-butoxy group, 3-methyl-c-butoxy group, 1,2-dimethyl-c-propoxy group, 2,3-dimethyl-c-propoxy group, 1-ethyl-c-propoxy group, 2-ethyl-c-propoxy group, n-hexyloxy group, 1-methyl-n-pentyloxy group, 2-methyl-n-pentyloxy group, 3-methyl-n-pentyloxy group, 4-methyl-n-pentyloxy group, 1,1-dimethyl-n-butoxy group, 1,2-dimethyl-n-butoxy group, 1,3-dimethyl-n-butoxy group, 2,2-dimethyl-n-butoxy group, 2,3-dimethyl-n-butoxy group, 3,3-dimethyl-n-butoxy group, 1-ethyl-n-butoxy group, 2-ethyl-n-butoxy group, 1,1,2-trimethyl-n-propoxy group, 1,2,2-trimethyl-n-propoxy group, 1-ethyl-1-methyl-n-propoxy group, 1-ethyl-2-methyl-n-propoxy group, c-hexyloxy group, 1-methyl-c-pentyloxy group, 2-methyl-c-pentyloxy group, 3-methyl-c-pentyloxy group, 1-ethyl-c-butoxy group, 2-ethyl-c-butoxy group, 3-ethyl-c-butoxy group, 1,2-dimethyl-c-butoxy group, 1,3-dimethyl-c-butoxy group, 2,2-dimethyl-c-butoxy group, 2,3-dimethyl-c-butoxy group, 2,4-dimethyl-c-butoxy group, 3,3-dimethyl-c-butoxy group, 1-n-propyl-c-propoxy group, 2-n-propyl-c-propoxy group, 1-i-propyl-c-propoxy group, 2-i-propyl-c-propoxy group, 1,2,2-trimethyl-c-propoxy group, 1,2,3-trimethyl-c-propoxy group, 2,2,3-trimethyl-c-propoxy group, 1-ethyl-2-methyl-c-propoxy group, 2-ethyl-1-methyl-c-propoxy group, 2-ethyl-2-methyl-c-propoxy group and 2-ethyl-3-methyl-c-propoxy group, etc.

$C_{1-6}$ alkoxycarbonyl group may be a straight-chain or branched alkoxycarbonyl group, or contain $C_{3-6}$ cycloalkoxycarbonyl group, and includes methoxycarbonyl group, ethoxycarbonyl group, n-propoxycarbonyl group, i-propoxycarbonyl group, c-propoxycarbonyl group, n-butoxycarbonyl group, i-butoxycarbonyl group, s-butoxycarbonyl group, t-butoxycarbonyl group, c-butoxycarbonyl group, 1-methyl-c-propoxycarbonyl group, 2-methyl-c-propoxycarbonyl group, n-pentyloxycarbonyl group, 1-methyl-n-butoxycarbonyl group, 2-methyl-n-butoxycarbonyl group, 3-methyl-n-butoxycarbonyl group, 1,1-dimethyl-n-propoxycarbonyl group, 1,2-dimethyl-n-propoxycarbonyl group, 2,2-dimethyl-n-propoxycarbonyl group, 1-ethyl-n-propoxycarbonyl group, c-pentyloxycarbonyl group, 1-methyl-c-butoxycarbonyl group, 2-methyl-c-butoxycarbonyl group, 3-methyl-c-butoxycarbonyl group, 1,2-dimethyl-c-propoxycarbonyl group, 2,3-dimethyl-c-propoxycarbonyl group, 1-ethyl-c-propoxycarbonyl group, 2-ethyl-c-propoxycarbonyl group, n-hexyloxycarbonyl group, 1-methyl-n-pentyloxycarbonyl group, 2-methyl-n-pentyloxycarbonyl group, 3-methyl-n-pentyloxycarbonyl group, 4-methyl-n-pentyloxycarbonyl group, 1,1-dimethyl-n-butoxycarbonyl group, 1,2-dimethyl-n-butoxycarbonyl group, 1,3-dimethyl-n-butoxycarbonyl group, 2,2-dimethyl-n-butoxycarbonyl group, 2,3-dimethyl-n-butoxycarbonyl group, 3,3-dimethyl-n-butoxycarbonyl group, 1-ethyl-n-butoxycarbonyl group, 2-ethyl-n-butoxycarbonyl group, 1,1,2-trimethyl-n-propoxycarbonyl group, 1,2,2-trimethyl-n-propoxycarbonyl group, 1-ethyl-1-methyl-n-propoxycarbonyl group, 1-ethyl-2-methyl-n-propoxycarbonyl group, c-hexyloxycarbonyl group, 1-methyl-c-pentyloxycarbonyl group, 2-methyl-c-pentyloxycarbonyl group, 3-methyl-c-pentyloxycarbonyl group, 1-ethyl-c-butoxycarbonyl group, 2-ethyl-c-butoxycarbonyl group, 3-ethyl-c-butoxycarbonyl group, 1,2-dimethyl-c-butoxycarbonyl group, 1,3-dimethyl-c-butoxycarbonyl group, 2,2-dimethyl-c-butoxycarbonyl group, 2,3-dimethyl-c-butoxycarbonyl group, 2,4-dimethyl-c-butoxycarbonyl group, 3,3-dimethyl-c-butoxycarbonyl group, 1-n-propyl-c-propoxycarbonyl group, 2-n-propyl-c-propoxycarbonyl group, 1-i-propyl-c-propoxycarbonyl group, 2-i-propyl-c-propoxycarbonyl group, 1,2,2-trimethyl-c-propoxycarbonyl group, 1,2,3-trimethyl-c-propoxycarbonyl group, 2,2,3-trimethyl-c-propoxycarbonyl group, 1-ethyl-2-methyl-c-propoxycarbonyl group, 2-ethyl-1-methyl-c-propoxycarbonyl group, 2-ethyl-2-methyl-c-propoxycarbonyl group and 2-ethyl-3-methyl-c-propoxycarbonyl group, etc.

$C_{1-6}$ alkylcarbonyloxy group may be a straight-chain or branched alkylcarbonyloxy group, or contain $C_{3-6}$ cycloalkylcarbonyloxy group, and includes methylcarbonyloxy group, ethylcarbonyloxy group, n-propylcarbonyloxy group, i-propylcarbonyloxy group, c-propylcarbonyloxy group, n-butylcarbonyloxy group, i-butylcarbonyloxy group, s-butylcarbonyloxy group, t-butylcarbonyloxy group, c-butylcarbonyloxy group, 1-methyl-c-propylcarbonyloxy group, 2-methyl-c-propylcarbonyloxy group, n-pentylcarbonyl group, 1-methyl-n-butylcarbonyloxy group, 2-methyl-n-butylcarbonyloxy group, 3-methyl-n-butylcarbonyloxy group, 1,1-dimethyl-n-propylcarbonyloxy group, 1,2-dimethyl-n-propylcarbonyloxy group, 2,2-dimethyl-n-propylcarbonyloxy group, 1-ethyl-n-propylcarbonyloxy group, c-pentylcarbonyl group, 1-methyl-c-butylcarbonyloxy group, 2-methyl-c-butylcarbonyloxy group, 3-methyl-c-butylcarbonyloxy group, 1,2-dimethyl-c-propylcarbonyloxy group, 2,3-dimethyl-c-propylcarbonyloxy group, 1-ethyl-c-propylcarbonyloxy group, 2-ethyl-c-propylcarbonyloxy group, n-hexylcarbonyloxy group, 1-methyl-n-pentylcarbonyloxy group, 2-methyl-n-pentylcarbonyloxy group, 3-methyl-n-pentylcarbonyloxy group, 4-methyl-n-pentylcarbonyloxy group, 1,1-dimethyl-n-butylcarbonyloxy group, 1,2-dimethyl-n-butylcarbonyloxy group, 1,3-dimethyl-n-butylcarbonyloxy group, 2,2-dimethyl-n-butylcarbonyloxy group, 2,3-dimethyl-n-butylcarbonyloxy group, 3,3-dimethyl-n-butylcarbonyloxy group, 1-ethyl-n-butylcarbonyloxy group, 2-ethyl-n-butylcarbonyloxy group, 1,1,2-trimethyl-n-propylcarbonyloxy group, 1,2,2-trimethyl-n-propylcarbonyloxy group, 1-ethyl-1-methyl-n-propylcarbonyloxy group, 1-ethyl-2-methyl-n-propylcarbonyloxy group, c-hexylcarbonyloxy group, 1-methyl-c-pentylcarbonyloxy group, 2-methyl-c-pentylcarbonyloxy group, 3-methyl-c-pentylcarbonyloxy group, 1-ethyl-c-butylcarbonyloxy group, 2-ethyl-c-butylcarbonyloxy group, 3-ethyl-c-butylcarbonyloxy group, 1,2-dimethyl-c-butylcarbonyloxy group, 1,3-dimethyl-c-butylcarbonyloxy group, 2,2-dimethyl-c-butylcarbonyloxy group, 2,3-dimethyl-c-butylcarbonyloxy group, 2,4-dimethyl-c-butylcarbonyloxy group, 3,3-dimethyl-c-butylcarbonyloxy group, 1-n-propyl-c-propylcarbonyloxy group, 2-n-propyl-c-propylcarbonyloxy group, 1-i-propyl-c-propylcarbonyloxy group, 2-i-propyl-c-propylcarbonyloxy group, 1,2,2-trimethyl-c-propylcarbonyloxy group, 1,2,3-trimethyl-c-propylcarbonyloxy group, 2,2,3-trimethyl-c-propylcarbonyloxy group, 1-ethyl-2-methyl-c-propylcarbonyloxy group, 2-ethyl-1-methyl-c-propylcarbonyloxy group, 2-ethyl-2-methyl-c-propylcarbonyloxy group and 2-ethyl-3-methyl-c-propylcarbonyloxy group, etc.

$C_{4-12}$ aromatic group includes 2-furyl group, 3-furyl group, 2-thienyl group, 3-thienyl group, phenyl group, α-naphthyl group, β-naphthyl group, o-biphenyl group, m-biphenyl group and p-biphenyl group, etc.

Next, specific examples of each substituent of $R^1$ and $R^2$ are described.

Specific examples of $R^1$ include methyl group, ethyl group, n-propyl group, i-propyl group, c-propyl group, n-butyl group, i-butyl group, s-butyl group, t-butyl group, c-butyl group, 1-methyl-c-propyl group, 2-methyl-c-propyl group, n-pentyl group, 1-methyl-n-butyl group, 2-methyl-n-butyl group, 3-methyl-n-butyl group, 1,1-dimethyl-n-propyl group, 1,2-dimethyl-n-propyl group, 2,2-dimethyl-n-propyl group, 1-ethyl-n-propyl group, c-pentyl group, 1-methyl-c-butyl group, 2-methyl-c-butyl group, 3-methyl-c-butyl group, 1,2-dimethyl-c-propyl group, 2,3-dimethyl-c-propyl group, 1-ethyl-c-propyl group, 2-ethyl-c-propyl group, n-hexyl group, 1-methyl-n-pentyl group, 2-methyl-n-pentyl group, 3-methyl-n-pentyl group, 4-methyl-n-pentyl group, 1,1-dimethyl-n-butyl group, 1,2-dimethyl-n-butyl group, 1,3-dimethyl-n-butyl group, 2,2-dimethyl-n-butyl group, 2,3-dimethyl-n-butyl group, 3,3-dimethyl-n-butyl group, 1-ethyl-n-butyl group, 2-ethyl-n-butyl group, 1,1,2-trimethyl-n-propyl group, 1,2,2-trimethyl-n-propyl group, 1-ethyl-1-methyl-n-propyl group, 1-ethyl-2-methyl-n-propyl group, c-hexyl group, 1-methyl-c-pentyl group, 2-methyl-c-pentyl group, 3-methyl-c-pentyl group, 1-ethyl-c-butyl group, 2-ethyl-c-butyl group, 3-ethyl-c-butyl group, 1,2-dimethyl-c-butyl group, 1,3-dimethyl-c-butyl group, 2,2-dimethyl-c-butyl group, 2,3-dimethyl-c-butyl group, 2,4-dimethyl-c-butyl group, 3,3-dimethyl-c-butyl group, 1-n-propyl-c-propyl group, 2-n-propyl-c-propyl group, 1-i-propyl-c-propyl group, 2-i-propyl-c-propyl group, 1,2,2-trimethyl-c-propyl group, 1,2,3-trimethyl-c-propyl group, 2,2,3-trimethyl-c-propyl group, 1-ethyl-2-methyl-c-propyl group, 2-ethyl-1-methyl-c-propyl group, 2-ethyl-2-methyl-c-propyl group, 2-ethyl-3-methyl-c-propyl group, c-heptyl group, c-octyl group, 2-furyl group, 3-furyl group, 2-thienyl group, 3-thienyl group, phenyl group, o-methylphenyl group, m-methylphenyl group, p-methylphenyl group, o-methoxyphenyl group, m-methoxyphenyl group, p-methoxyphenyl group, o-benzyloxyphenyl group, m-benzyloxyphenyl group, p-benzyloxyphenyl group, o-chlorophenyl group, m-chlorophenyl group, p-chlorophenyl group, o-bromophenyl group, m-bromophenyl group, p-bromophenyl group, α-naphthyl group, β-naphthyl group and benzyl group etc., and particularly n-propyl group, i-propyl group, t-butyl group, c-pentyl group, c-hexyl group, c-hepty group, phenyl group, p-benzyloxyphenyl group, m-methylphenyl group, p-methylphenyl group, β-naphthyl group, p-bromophenyl group and 2-furyl group.

Specific examples of $R^2$ include methyl group, ethyl group, n-propyl group, i-propyl group, c-propyl group, n-butyl group, i-butyl group, s-butyl group, t-butyl group, c-butyl group, 1-methyl-c-propyl group, 2-methyl-c-propyl group, n-pentyl group, 1-methyl-n-butyl group, 2-methyl-n-butyl group, 3-methyl-n-butyl group, 1,1-dimethyl-n-propyl group, 1,2-dimethyl-n-propyl group, 2,2-dimethyl-n-propyl group, 1-ethyl-n-propyl group, c-pentyl group, 1-methyl-c-butyl group, 2-methyl-c-butyl group, 3-methyl-c-butyl group, 1,2-dimethyl-c-propyl group, 2,3-dimethyl-c-propyl group, 1-ethyl-c-propyl group, 2-ethyl-c-propyl group, n-hexyl group, 1-methyl-n-pentyl group, 2-methyl-n-pentyl group, 3-methyl-n-pentyl group, 4-methyl-n-pentyl group, 1,1-dimethyl-n-butyl group, 1,2-dimethyl-n-butyl group, 1,3-dimethyl-n-butyl group, 2,2-dimethyl-n-butyl group, 2,3-dimethyl-n-butyl group, 3,3-dimethyl-n-butyl group, 1-ethyl-n-butyl group, 2-ethyl-n-butyl group, 1,1,2-trimethyl-n-propyl group, 1,2,2-trimethyl-n-propyl group, 1-ethyl-1-methyl-n-propyl group, 1-ethyl-2-methyl-n-propyl group, c-hexyl group, 1-methyl-c-pentyl group, 2-methyl-c-pentyl group, 3-methyl-c-pentyl group, 1-ethyl-c-butyl group, 2-ethyl-c-butyl group, 3-ethyl-c-butyl group, 1,2-dimethyl-c-butyl group, 1,3-dimethyl-c-butyl group, 2,2-dimethyl-c-butyl group, 2,3-dimethyl-c-butyl group, 2,4-dimethyl-c-butyl group, 3,3-dimethyl-c-butyl group, 1-n-propyl-c-propyl group, 2-n-propyl-c-propyl group, 1-i-propyl-c-propyl group, 2-i-propyl-c-propyl group, 1,2,2-trimethyl-c-propyl group, 1,2,3-trimethyl-c-propyl group, 2,2,3-trimethyl-c-propyl group, 1-ethyl-2-methyl-c-propyl group, 2-ethyl-1-methyl-c-propyl group, 2-ethyl-2-methyl-c-propyl group, 2-ethyl-3-methyl-c-propyl group, c-heptyl group, c-octyl group, phenyl group and benzyl group etc., and particularly methyl group and benzyl group.

Preferable α-aminoacyl acetic acid ester compounds of formula (1) include the following:

1) α-aminoacyl acetic acid ester compounds of formula (1) wherein $R^1$ is $C_{1-20}$ alkyl group or $C_{4-12}$ aromatic group (the aromatic group may be arbitrarily substituted with halogen atom, $C_{1-6}$ alkyl group, $C_{1-6}$ alkoxy group or benzyloxy group);

2) α-aminoacyl acetic acid ester compounds of formula (1) wherein $R^2$ is $C_{1-6}$ alkyl group, or $C_{1-6}$ alkyl group substituted with $C_{4-12}$ aromatic group;

3) α-aminoacyl acetic acid ester compounds of formula (1) wherein $R^1$ is $C_{1-20}$ alkyl group or $C_{4-12}$ aromatic group (the aromatic group may be arbitrarily substituted with halogen atom, $C_{1-6}$ alkyl group, $C_{1-6}$ alkoxy group or benzyloxy group), and $R^2$ is $C_{1-6}$ alkyl group, or $C_{1-6}$ alkyl group substituted with $C_{4-12}$ aromatic group;

4) α-aminoacyl acetic acid ester compounds of formula (1) wherein $R^1$ is n-propyl group, i-propyl group, t-butyl group, c-pentyl group, c-hexyl group, c-hepty group, phenyl group, p-benzyloxyphenyl group, m-methylphenyl group, p-methylphenyl group, β-naphthyl group, p-bromophenyl group or 2-furyl group;

5) α-aminoacyl acetic acid ester compounds of formula (1) wherein $R^2$ is methyl group or benzyl group; and 6) α-aminoacyl acetic acid ester compounds of formula (1) wherein $R^1$ is n-propyl group, i-propyl group, t-butyl group, c-pentyl group, c-hexyl group, c-hepty group, phenyl group, p-benzyloxyphenyl group, m-methylphenyl group, p-methylphenyl group, β-naphthyl group, p-bromophenyl group or 2-furyl group, and $R^2$ is methyl group or benzyl group.

As the catalyst used for the catalytic asymmetric hydrogenation in the present invention, catalysts that are utilized in general catalytic asymmetric hydrogenation can be used (see, Non-patent Document 3).

Preferable catalysts include a complex of a Group VIII transition metal of the Periodic Table having an optically active phosphine ligand.

The Group VIII transition metal of the Periodic Table includes iron, cobalt, nickel, ruthenium, rhodium, palladium, osmium, iridium and platinum, and ruthenium, rhodium and iridium are preferable.

All of the optically active phosphine ligands used in the present invention become optically active forms. As the optically active phosphine ligand, optically active bidentate phosphine ligands are preferable. The optically active bidentate phosphine ligands include BINAP, BIPHEMP, RROPHOS, DEGUPHOS, DIOP, DIPAMP, DuPHOS, NORPHOS, PNNP, SKEWPHOS, BPPFA, SEGPHOS, CHIRAPHOS and $H_8$-BINAP, etc.

BINAP includes also the derivatives of BINAP, and specific examples thereof are 2,2'-bis(diphenylphosphino)-1,1'-binaphthyl, 2,2'-bis(di-p-tolylphosphino)-1,1'-binaphthyl, 2,2'-bis(di-p-t-butylphenylphosphino)-1,1'-binaphthyl, 2,2'-bis(di-m-tolylphosphino)-1,1'-binaphthyl, 2,2'-bis(di-3,5-dimethylphenylphosphino)-1,1'-binaphthyl, 2,2'-bis(di-p-methoxyphenylphosphino)-1,1'-binaphthyl, 2,2'-bis(dicyclopentylphosphino)-1,1'-binaphthyl, 2,2'-bis(dicyclohexylphosphino)-1,1'-binaphthyl, 2-di(β-naphthyl)phosphino-2'-diphenylphosphino-1,1'-binaphthyl and 2-diphenylphosphino-2'-di(p-trifluoromethylphenyl)phosphino-1,1'-binaphthyl, etc., and preferably 2,2'-bis(diphenylphosphino)-1,1'-binaphthyl, 2,2'-bis(di-p-tolylphosphino)-1,1'-binaphthyl and 2,2'-bis(di-p-t-butylphenylphosphino)-1,1'-binaphthyl.

BIPHEMP includes also the derivatives of BIPHEMP, and specific examples thereof are 2,2'-dimethyl-6,6'-bis(diphenylphosphino)-1,1'-biphenyl, 2,2'-dimethyl-6,6'-bis(dicyclohexylphosphino)-1,1'-biphehyl, 2,2'-dimethyl-4,4'-bis(dimethylamino)-6,6'-bis(diphenylphosphino)-1,1'-biphenyl, 2,2',4,4'-tetramethyl-6,6'-bis(diphenylphosphino)-1,1'-biphenyl, 2,2'-dimethoxy-6,6'-bis(diphenylphosphino)-1,1'-biphenyl, 2,2',3,3'-tetramethoxy-6,6'-bis(diphenylphosphino)-1,1'-biphenyl, 2,2',4,4'-tetramethyl-3,3'-dimethoxy-6,6'-bis(diphenylphosphino)-1,1'-biphenyl, 2,2'-dimethyl-6,6'-bis(di-p-tolylphosphino)-1,1'-biphenyl, 2,2'-dimethyl-6,6'-bis(di-t-butylphenylphosphino)-1,1'-biphenyl and 2,2',4,4'-tetramethyl-3,3'-dimethoxy-6,6'-bis(di-p-methoxyphenylphosphino)-1,1'-biphenyl, etc., and preferably 2,2'-dimethyl-6,6'-bis(diphenylphosphino)-1,1'-biphenyl.

Examples of other optically active bidentate phosphine ligands and the derivatives thereof are illustrated below, but the present invention is not limited thereto.

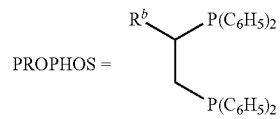

PROPHOS: $R^b$ = $CH_3$
BENZPHOS: $R^b$ = $C_6H_5CH_2$
CyCPHOS: $R^b$ = c-$C_6H_{11}$

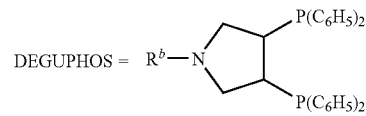

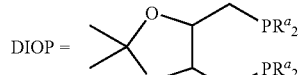

DIOP: $R^a$ = $C_6H_5$
CyDIOP: $R^a$ = c-$C_6H_{11}$

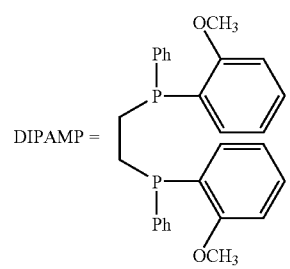

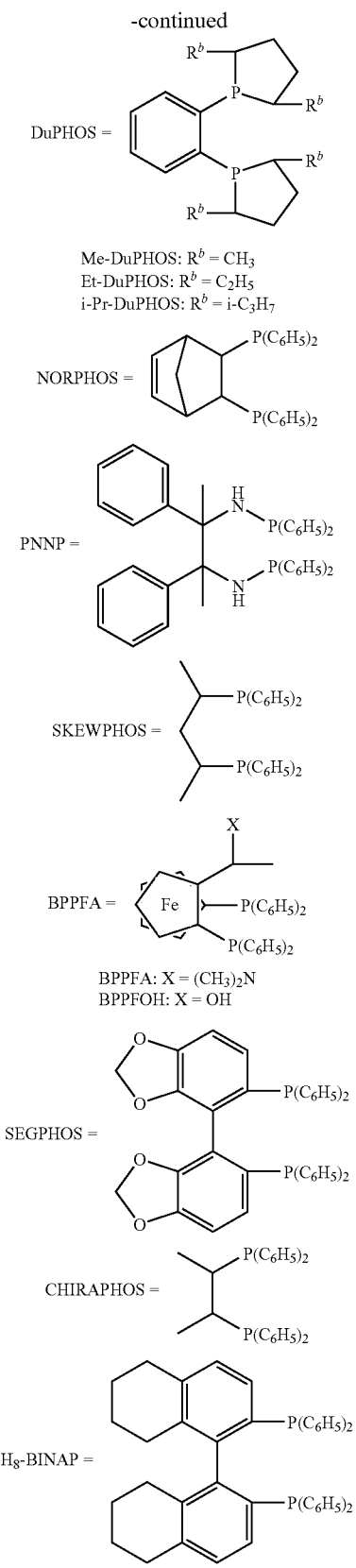

The catalyst used for the catalytic asymmetric hydrogenation in the present invention can be prepared from a transition metal compound and an optically active phosphine ligand, and an additive that is able to be coordinated can be optionally added.

The transition metal compound includes a rhodium compound such as di-p-chlorotetrakis(cyclooctene) 2 rhodium, di-μ-chlorobis(1,5-cyclooctadiene) 2 rhodium and 1,5-cyclooctadiene bis(acetonitrile)rhodium tetrafluoroborate, etc., an iridium compound such as di-g-chlorotetrakis(cyclooctene) 2 iridium, di-μ-chlorobis(1,5-cyclooctadiene) 2 rhodium, di-Wchlorotetrakis(ethylene) 2 iridium and 1,5-cyclooctadiene bis(acetonitrile)iridium tetrafluoroborate, etc., a ruthenium compound such as tetrachloro(η-benzene) 2 ruthenium and tetrachloro[η-(p-cymene)]2 ruthenium, etc.

The additives are not specifically limited so long as they are compounds that can be coordinated, and for example in case where a ruthenium compound is used, N,N-dimethylformamide or the like is preferable, and in case where an iridium compound is used, an iodine compound is preferable.

Specific examples of the iodine compound are tetramethyl ammonium iodide, tetra n-butyl ammonium iodide, sodium iodide and potassium iodide, etc., and preferably sodium iodide.

The used amount of the optically active phosphine ligand is 1 equivalent or more, preferably 1 to 2 equivalents, more preferably 1.1 to 1.5 equivalent in case of optically active bidentate phosphine ligand based on the amount of the transition metal compound.

In the meanwhile, in the catalyst used in the catalytic asymmetric hydrogenation in which a transition metal compound and an optically active bidentate phosphine ligand are used in a proportion of 1:2, 2 times the above-mentioned used amount is used. In addition, in case where an optically active monodentate phosphine ligand is used, 2 times the above-mentioned used amount is used because of difference in valency.

The used amount of the additive optionally added cannot be necessarily determined because it depends on the compositional ratio of the catalyst, but it generally ranges from 1 to 100 equivalents, preferably 1 to 10 equivalents based on the used amount of the transition metal compound.

It is preferable to carry out the preparation of a catalyst used for catalytic asymmetric hydrogenation in the presence of an inert gas such as argon.

The ruthenium catalyst among the catalysts used for catalytic asymmetric hydrogenation is described in further detail.

Ruthenium-optically active phosphine complex includes ruthenium-BINAP complex, ruthenium-BIPHEMP complex, ruthenium-RROPHOS complex, ruthenium-DEGUPHOS complex, ruthenium-DIOP complex, ruthenium-DIPAMP complex, ruthenium-DuPHOS complex, ruthenium-NORPHOS complex, ruthenium-PNNP complex, ruthenium-SKEWPHOS complex, ruthenium-BPPFA complex, ruthenium-SEGPHOS complex, ruthenium-CHIRAPHOS complex and ruthenium-$H_8$-BINAP complex, etc.

Hereinafter, ruthenium-BINAP complexes are described in detail, but other optically active phosphine ligands can be used similarly.

The ruthenium-BINAP complexes include $RuHX^1(R^3\text{-BINAP})_2$, $RuX^2{}_2(R^3\text{-BINAP})$ or $Ru_2Cl_4(R^3\text{-BINAP})_2(Et_3N)$ wherein $X^1$ and $X^2$ independently of each other are Cl, $ClO_4$, $BF_4$, $PF_6$, $OCOCH_3$, $OCOCF_3$, OCO-t-Bu or $OSO_2CF_3$, $R^3$-BINAP is

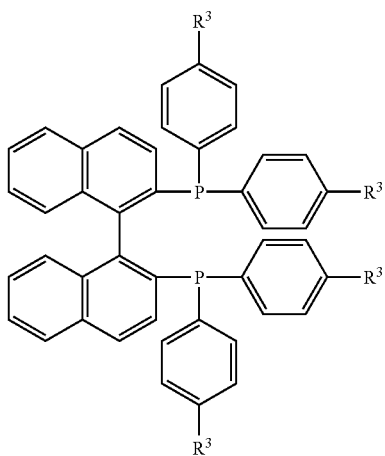

wherein $R^3$ is hydrogen atom, methyl group or t-butyl group, absolute configuration is either S or R, the complex may be further coordinated with N,N-dimethylformamide, benzene, $AlCl_3$, $SnCl_4$, $TiCl_4$ or $ZnCl_2$, and specifically RuHCl(BINAP)$_2$, RuHCl(T-BINAP)$_2$, RuHCl(t-Bu-BINAP)$_2$, RuH(ClO$_4$)(BINAP)$_2$, RuH(ClO$_4$)(T-BINAP)$_2$, RuH(BF$_4$)(BINAP)$_2$, RuH(BF$_4$)(T-BINAP)$_2$, RuH(PF$_6$)(BINAP)$_2$, RuH(PF$_6$)(T-BINAP)$_2$, RuCl$_2$(BINAP), RuCl$_2$(T-BINAP), RuCl$_2$(t-Bu-BINAP), RuCl$_2$(BINAP)(dmf)$_n$, RuCl$_2$(T-BINAP)(dmf)$_n$, RuCl$_2$(t-Bu-BINAP)(dmf)$_n$, RuCl$_2$(BINAP)(C$_6$H$_6$)$_n$, RuCl$_2$(T-BINAP) (C$_6$H$_6$)$_n$, RuCl$_2$(t-Bu-BINAP)(C$_6$H$_6$)$_n$, Ru(ClO$_4$)$_2$(BINAP), Ru(ClO$_4$)$_2$(T-BINAP), Ru(ClO$_4$)$_2$(t-Bu-BINAP), Ru(BF$_4$)$_2$(BINAP), Ru(BF$_4$)$_2$(T-BINAP), Ru(BF$_4$)$_2$(t-Bu-BINAP), Ru(PF$_6$)$_2$(BINAP), Ru(PF$_6$)$_2$(T-BINAP), Ru(OCOCH$_3$)$_2$(BINAP), Ru(OCOCF$_3$)$_2$(BINAP), Ru(OCO-t-Bu)$_2$(BINAP), Ru(OCOCH$_3$)$_2$(T-BINAP), Ru(OCOCF$_3$)$_2$(T-BINAP), Ru(OCOCH$_3$)$_2$(t-Bu-BINAP), Ru(OCOCH$_3$)$_2$(BINAP)(ZnCl$_2$), Ru(OCOCH$_3$)$_2$(BINAP) (AlCl$_3$), Ru(OCOCH$_3$)$_2$(BINAP)(SnCl$_4$), Ru(OCOCH$_3$)$_2$(BINAP)(TiCl$_4$), Ru(OCOCH$_3$)$_2$(T-BINAP)(ZnCl$_2$), Ru(OCOCH$_3$)$_2$(T-BINAP) (AlCl$_3$), Ru(OCOCH$_3$)$_2$(T-BINAP)(SnCl$_4$), Ru(OCOCH$_3$)$_2$(T-BINAP)(TiCl$_4$), Ru$_2$Cl$_4$(BINAP)$_2$(Et$_3$N), Ru$_2$Cl$_4$(T-BINAP)$_2$(Et$_3$N), Ru$_2$Cl$_4$(t-Bu-BINAP)$_2$(Et$_3$N), Ru$_2$Cl$_4$(BINAP)$_2$(ZnCl$_2$)$_2$(Et$_3$N), Ru$_2$Cl$_4$(BINAP)$_2$(AlCl$_3$)$_2$(Et$_3$N), Ru$_2$Cl$_4$(BINAP)$_2$(SnCl$_4$)$_2$(Et$_3$N), Ru$_2$Cl$_4$(BINAP)$_2$(TiCl$_4$)$_2$(Et$_3$N), Ru$_2$Cl$_4$(T-BINAP)$_2$(ZnCl$_2$)$_2$(Et$_3$N), Ru$_2$Cl$_4$(T-BINAP)$_2$(AlCl$_3$)$_2$(Et$_3$N), Ru$_2$Cl$_4$(T-BINAP)$_2$(SnCl$_4$)$_2$(Et$_3$N) and Ru$_2$Cl$_4$(T-BINAP)$_2$(TiCl$_4$)$_2$(Et$_3$N), wherein BINAP is bis(diphenylphosphino)-1,1'-binaphthyl in absolute configuration of S or R, T-BINAP is 2,2'-bis(di-p-tolylphosphino)-1,1'-binaphthyl in absolute configuration of S or R, t-Bu-BINAP is 2,2'-bis(di-p-t-butylphenylphosphino)-1,1'-binaphthyl in absolute configuration of S or R, Et is ethyl group, t-Bu is t-butyl group, dmf is N,N-dimethylformamide, n is 1 or 2.

Preferable ruthenium-optically active phosphine complexes include the following 1) and 2):

1) RuHX$^1$ (R$^3$-BINAP)$_2$, RuX$^2_2$(R$^3$-BINAP) or Ru$_2$Cl$_4$(R$^3$-BINAP)$_2$(Et$_3$N) wherein X$^1$ and X$^2$ independently of each other are Cl, ClO$_4$, BF$_4$, PF$_6$, OCOCH$_3$, OCOCF$_3$, OCO-t-Bu or OSO$_2$CF$_3$, R$^3$-BINAP is

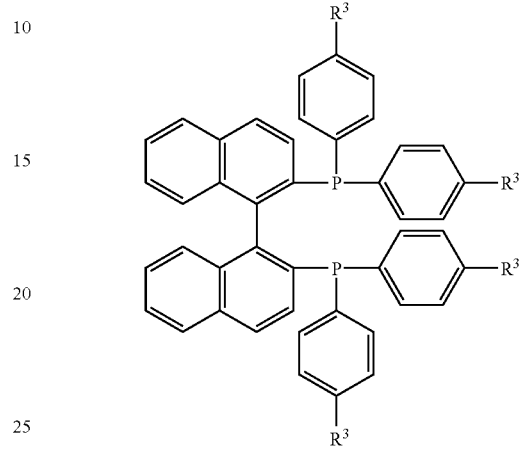

wherein $R^3$ is hydrogen atom, methyl group or t-butyl group, absolute configuration is either S or R, the complex may be further coordinated with N,N-dimethylformamide, benzene, $AlCl_3$, $SnCl_4$, $TiCl_4$ or $ZnCl_2$; and 2) RuCl$_2$(BINAP)$_2$, RuCl$_2$(T-BINAP), RuCl$_2$(t-Bu-BINAP), RuCl$_2$(BINAP)(dmf)$_n$, RuCl$_2$(T-BINAP)(dmf)$_n$, RuCl$_2$(t-Bu-BINAP)(dmf)$_n$, RuCl$_2$(BINAP)(C$_6$H$_6$)$_n$, RuCl$_2$(T-BINAP) (C$_6$H$_6$)$_n$ or RuCl$_2$(t-Bu-BINAP)(C$_6$H$_6$)$_n$ wherein BINAP is 2,2'-bis(diphenylphosphino)-1,1'-binaphthyl in absolute configuration of S or R, T-BINAP is 2,2'-bis(di-p-tolylphosphino)-1,1'-binaphthyl in absolute configuration of S or R, t-Bu-BINAP is 2,2'-bis(di-p-t-butylphenylphosphino)-1,1'-binaphthyl in absolute configuration of S or R, dmf is N,N-dimethylformamide, n is 1 or 2.

The ruthenium-optically active phosphine complexes of 1) are preferably RuX$^2_2$(R$^3$-BINAP) wherein X$^2$ and R$^3$-BINAP have the same meaning as the above, the complex may be further coordinated with N,N-dimethylformamide, benzene, AlCl$_3$, SnCl$_4$, TiCl$_4$ or ZnCl$_2$, more preferably RuX$^2_2$ (R$^3$-BINAP) further coordinated with N,N-dimethylformamide or benzene wherein X$^2$ is Cl, R$^3$-BINAP has the same meaning as the above.

The ruthenium-optically active phosphine complexes of 2) are preferably RuCl$_2$(BINAP)(dmf)$_n$, RuCl$_2$(T-BINAP)(dmf)$_n$ or RuCl$_2$(t-Bu-BINAP)(dmf)$_n$ wherein BINAP is 2,2'-bis(diphenylphosphino)-1,1'-binaphthyl in absolute configuration of S or R, T-BINAP is 2,2'-bis(di-p-tolylphosphino)-1, 1'-binaphthyl in absolute configuration of S or R, t-Bu-BINAP is 2,2'-bis(di-p-t-butylphenylphosphino)-1,1'-binaphthyl in absolute configuration of S or R, dmf is N,N-dimethylformamide, n is 1 or 2, more preferably RuCl$_2$ (BINAP)(dmf)$_n$ wherein BINAP is 2,2'-bis(diphenylphosphino)-1,1'-binaphthyl in absolute configuration of S or R, dmf is N,N-dimethylformamide, n is 1 or 2.

The iridium catalyst among the catalysts used for catalytic asymmetric hydrogenation is described in further detail.

Iridium-optically active phosphine complex includes iridium-BINAP complex, iridium-BIPHEMP complex, iridium-RROPHOS complex, iridium-DEGUPHOS complex, iridium-DIOP complex, iridium-DIPAMP complex, iridium-DuPHOS complex, iridium-NORPHOS complex, iridium-PNNP complex, iridium-SKEWPHOS complex, iridium-BPPFA complex, iridium-SEGPHOS complex, iridium-CHIRAPHOS complex and iridium-$H_8$-BINAP complex, etc.

Preferable iridium-optically active phosphine complex includes iridium-BINAP complex or iridium-BIPHEMP complex.

As the iridium-BINAP complex, the complex in which BINAP is BINAP, T-BINAP or t-Bu-BINAP is preferable. When the complex is prepared, it is preferable to add an iodine compound as an additive.

As the iridium-BIPHEMP complex, the complex in which BIPHEMP is 2,2'-dimethoxy-6,6'-bis(diphenylphosphino)-1,1'-biphenyl(MeO-Biphep) is preferable. When the complex is prepared, it is preferable to add an iodine compound as an additive, and particularly sodium iodide or tetra n-butylammonium iodide as the iodine compound.

Further, when the iridium-BINAP complex or the iridium-BIPHEMP complex is prepared, it is preferable to add [Ir(cod)Cl]$_2$ wherein cod is 1,5-cyclooctadiene, particularly to use further sodium iodide as an additive in an amount of 1 to 3 equivalents based on the used amount of iridium.

The rhodium catalyst among the catalysts used for catalytic asymmetric hydrogenation is described in further detail.

Rhodium-optically active phosphine complex includes rhodium-BINAP complex, rhodium-BIPHEMP complex, rhodium-RROPHOS complex, rhodium-DEGUPHOS complex, rhodium-DIOP complex, rhodium-DIPAMP complex, rhodium-DuPHOS complex, rhodium-NORPHOS complex, rhodium-PNNP complex, rhodium-SKEWPHOS complex, rhodium-BPPFA complex, rhodium-SEGPHOS complex, rhodium-CHIRAPHOS complex and rhodium-$H_8$-BINAP complex, etc.

BEST MODE FOR CARRYING OUT THE INVENTION

The process for producing optically active β-hydroxy-α-aminocarboxylic acid derivative of the present invention is described.

As shown in the scheme below, an optically active β-hydroxy-α-aminocarboxylic acid derivative of formula (2) or (3) can be produced by reducing an α-aminoacyl acetic acid ester compound of formula (1) with hydrogen in the presence of a catalyst used for catalytic asymmetric hydrogenation and an acid:

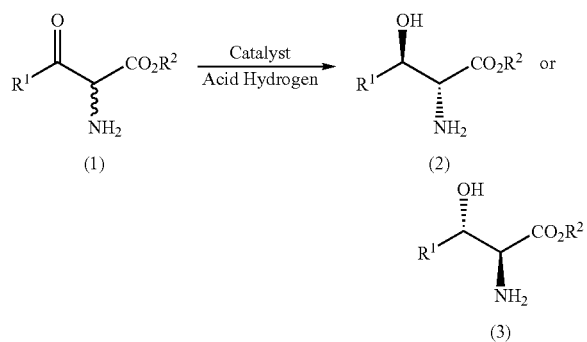

Generally, the above-mentioned reaction is carried out in a solvent. The solvent is not specifically limited so long as it does not pertain to the reaction, and includes for example halogen-type solvents such as 1,1-dichloroethane, 1,2-dichloroethane, methylene chloride, chloroform, chlorobenzene and 1,2-dichlorobenzene or the like, ether-type solvents such as diethyl ether, diisopropyl ether, tetrahydrofuran, or the like, alcohol-type solvent such as methanol, ethanol, n-propanol, i-propanol, 2-butanol, and ethylene glycol or the like, acetic acid and arbitrary mixed solvents of the above-mentioned solvents.

Preferable solvents include a halogen-type solvent, an alcohol-type solvent, a mixed solvent of a halogen-type solvent with an alcohol-type solvent, a mixed solvent of a halogen-type solvent with an ether-type solvent, acetic acid, a mixed solvent of acetic acid with an alcohol-type solvent, and a mixed solvent of acetic acid with an ether-type solvent, and for example methanol, n-propanol, i-propanol, 2-butanol, ethylene glycol, methylene chloride, 1,2-dichloroethane, chlorobenzene, methanol-methylene chloride, n-propanol-methylene chloride, i-propanol-methylene chloride, n-propanol-tetrahydrofuran, acetic acid, acetic acid-i-propanol and acetic acid-tetrahydrofuran, etc., and preferably methylene chloride, n-propanol, n-propanol-methylene chloride and acetic acid, etc.

In addition, in case where the ruthenium catalyst is used, it is preferable to use methylene chloride, n-propanol, n-propanol-methylene chloride or the like. In case where the iridium catalyst is used, it is preferable to use acetic acid.

The used amount of the catalyst for catalytic asymmetric hydrogenation is a range of 0.01 to 100 mol % based on the used amount of α-aminoacyl acetic acid ester compound of formula (1). It is preferably a range of 0.01 to 20 mol %, more preferably a range of 0.1 to 10 mol %, the most preferably 0.3 to 5 mol % from the standpoint of reaction efficiency and cost.

Although an α-aminoacyl acetic acid ester compound of formula (1) may be added in a solution in which an acid is present, a salt previously prepared from an α-aminoacyl acetic acid ester compound of formula (1) and an acid may be added in a solution. From the standpoint of the stability of α-aminoacyl acetic acid compounds of formula (1), it is preferable to previously prepare a salt composed of an α-aminoacyl acetic acid ester compound of formula (1) and an acid and add the salt in a solution.

The used acid is preferably a strong acid. The specific examples of the strong acid are HCl, HBr, $H_2SO_4$, $HClO_4$, $CH_3SO_3H$, $PhSO_3H$, TsOH, $CF_3SO_3H$ and $CF_3CO_2H$, etc., preferably HCl and TsOH, more preferably HCl.

The used amount of the acid is a range of 0.8 to 3 mol %, preferably a range of 0.9 to 2 mol %, more preferably a range of 0.9 to 1.5 mol % based on the used amount of α-aminoacyl acetic acid ester compound of formula (1). In the meanwhile, when a salt previously prepared from an α-aminoacyl acetic acid ester compound of formula (1) and an acid is added, the used amount of the acid means the total amount involving acids contained in the salt.

In addition, an acetic acid salt may be added in the reaction system. The acetic acid salt includes an alkali metal acetate such as lithium acetate, sodium acetate and potassium acetate, etc., and ammonium acetate, etc., and preferably an alkali metal acetate such as sodium acetate.

The used amount of the acetic acid salt is a range of 0.8 to 5 equivalents, preferably a range of 0.8 to 2 equivalents based on the used amount of α-aminoacyl acetic acid ester compound of formula (1). In particular, when the iridium catalyst is used, it is preferable to add an acetic acid salt.

The used hydrogen is generally hydrogen gas. The pressure of the used hydrogen is generally a range of 1 to 150 atm, preferably a range of 10 to 150 atm, more preferably 30 to 100 atm.

The reaction can be carried out at a reaction temperature ranging from 0° C. to a boiling point of the solvent, preferably from 10° C. to 150° C., more preferably 30° C. to 100° C.

The reaction time is not necessarily determined because it varies depending on the reaction temperature, but for example a reaction time of 4 hours or more in case where the reaction temperature is 50° C., and a reaction time of 3 hours or more in case where the reaction temperature is 100° C. are satisfactory.

After the completion of the reaction, an aimed optically active β-hydroxy-α-aminocarboxylic acid derivative can be obtained in a form of salt by concentrating the solvent. In addition, an aimed optically active β-hydroxy-α-aminocarboxylic acid derivative can be obtained by making the reaction solution basic and extracting with a suitable solvent. Further, an optically active β-hydroxy-α-aminocarboxylic acid derivative of formula (2) or (3) can be isolated in a high purity by purifying by distillation, recrystallization and silica gel column chromatography, etc.

Diastereo selectivity (de: selectivity of syn form and anti form) and enantio selectivity (ee) of the optically active β-hydroxy-α-aminocarboxylic acid derivative of formula (2) or (3) obtained in the present invention can be determined by performing instrumental analysis after benzoylation of the resulting optically active β-hydroxy-α-aminocarboxylic acid derivative.

The process of the benzoylation is as follows:

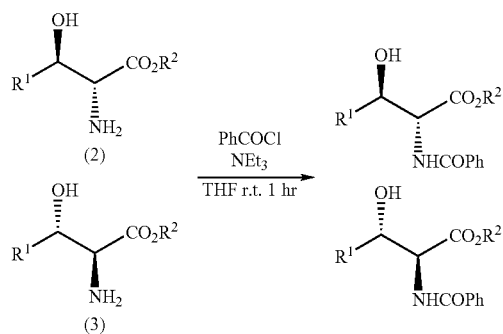

That is, the benzoylated compound of the optically active β-hydroxy-α-aminocarboxylic acid derivative of formula (2) or (3) can be produced by reacting the optically active β-hydroxy-α-aminocarboxylic acid derivative of formula (2) or (3) or the salt thereof with PhCOCl (benzoyl chloride) in THF (tetrahydrofuran) in the presence of NEt₃ (triethylamine). After purification of the resulting benzoylated compound, diastereo selectivity (de: selectivity of syn form and anti form) thereof can be determined with ¹H-NMR or the like and enantio selectivity (ee) thereof can be determined with HPLC analysis or the like.

The α-aminoacyl acetic acid ester compound of formula (1) being a starting material can be produced by a process shown below.

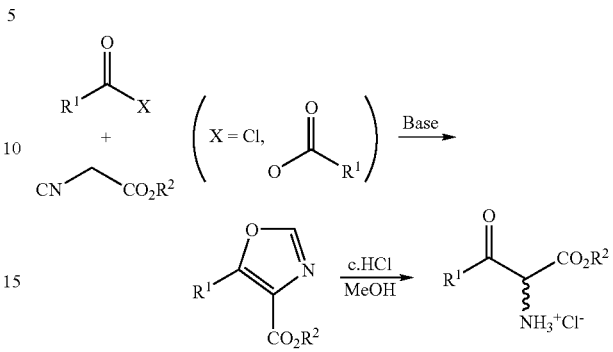

That is, the hydrochloride of the α-aminoacyl acetic acid ester compound of formula (1) can be produced by condensing an acid anhydride or acyl chloride and an isonitrile acetate in the presence of a base (the base includes triethyl amine, 1,8-diazabicyclo[5.4.0]undeca-7-ene or the like) to obtain an oxazole compound and then cleaving the oxazole ring with concentrated hydrochloric acid. The resulting hydrochloride can be used as such for the following reduction reaction, and can be processed with a base or the like to obtain the α-aminoacyl acetic acid ester compound of formula (1). In addition, in order to obtain the salt with other acid, the oxazole compound is cleft with other acid or the hydrochloride is subjected to salt exchange with other acid.

The hydrochloride of the α-aminoacyl acetic acid ester compound of formula (1) can be produced also by a process shown below:

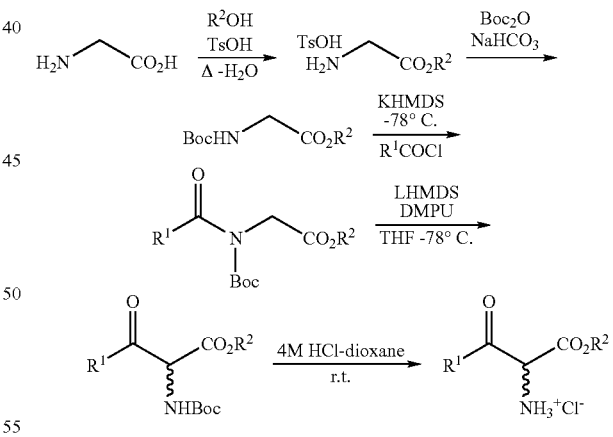

That is, the hydrochloride of the α-aminoacyl acetic acid ester compound of formula (1) can be produced by dehydrating and condensing glycine with an alcohol in the presence of TsOH (p-toluenesulfonic acid) to obtain an ester, subjecting the amino group to t-butoxycarbonylation with Boc₂O (di-t-butyl dicarbonate), treating with KHMDS (potassium hexamethyl disilazide), subjecting to amidation by adding acyl chloride, and carrying out rearrangement reaction by treating with LHMDS (lithium hexamethyl disilazide) and DMPU (1,3-dimethyl-3,4,5,6-perhydropyrimidine-2-one) to obtain Boc form of the α-aminoacyl acetic acid ester compound, then removing Boc with hydrochloric acid.

EXAMPLES

Hereinafter, the present invention is described based on examples to which the present invention is not limited at all.

Reference Example 1

Production of 2-cyclohexyl-1-methoxycarbonyl-2-oxo-ethyl-ammonium; chloride

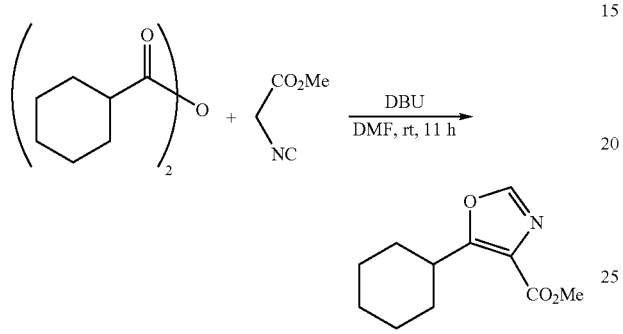

To DMF (N,N-dimethylformamide) (10.0 mL) solution of methylisocyanoate (3.11 g) and cyclohexanoic acid anhydride (8.20 g, 1.1 equivalent), DBU (1,8-diazabicyclo[5.4.0]-7-undecene) (4.7 mL, 1.0 equivalent) was added dropwise at 0° C. After stirring at room temperature for 11 hours, the reaction solution was diluted with water, extracted with n-hexane-ethyl acetate (5:1), and the organic phase was separated. Then, the organic phase was washed with saturated salt water, 1 mol/L hydrochloric acid, saturated sodium hydrogen carbonate water and saturated salt water in that order, and then dried over anhydrous sodium sulfate. Then, precipitates were filtered, and the filtrate was concentrated under reduced pressure. The resulting crude product was recrystallized from n-hexane-ethyl acetate to obtain a product (5.00 g, 75%).

Melting point: 97.5-101° C.

IR (KBr) 2931, 2852, 1719, 1599, 1199 cm$^{-1}$;

1H-NMR (400 MHz, CDCl$_3$) δ 1.26-1.89 (m, 10H, c-Hex-CH$_2$), 3.45-3.48 (m, 1H, c-Hex-H), 3.91 (s, 3H, CO$_2$CH$_3$), 7.74 (s, 1H, OCHN);

$^{13}$C-NMR (100 MHz, CDCl$_3$) δ 25.7, 25.9, 30.6, 35.4, 51.9, 125.2, 148.6, 162.6, 164.1;

HRMS (FAB, NBA) Calcd. for C$_{11}$H$_{16}$NO$_3$: 210.1130 (M$^+$+1).

Found: 210.1119.

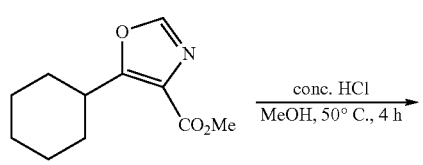

Oxazole (10 mmol) was dissolved in concentrated hydrochloric acid (5.0 mL) and methanol (15.0 mL). The resulting solution was stirred at 50° C. for 4 hours. Then, the reaction solution was cooled to room temperature, and concentrated. The residue was pulverized in diethylether, and an α-amino-β-ketoester was filtered off. The solid was used in the subsequent step as such. (Yield: 67%)

IR (KBr) 2931, 2856, 1752, 1719, 1560, 1508, 1458, 1276, 1144 cm$^{-1}$;

1H-NMR (400 MHz, CDCl$_3$) δ 1.19-1.50 (m, 5H, c-Hex-H), 1.66-1.82 (m, 4H, c-Hex-H), 2.18-2.20 (m, 1H, c-Hex-H), 2.90-2.95 (m, 1H, c-Hex-H), 3.91 (s, 3H, CO$_2$CH$_3$), 5.50 (s, COCHNH$_3$), 8.92 (br, COCHNH$_3$);

$^{13}$C-NMR (100 MHz, CDCl$_3$) δ 25.0, 25.6, 25.7, 27.4, 29.2, 48.4, 54.2, 60.3, 163.8, 201.0;

HRMS (FAB, NBA) Calcd. for C$_{10}$H$_{16}$NO$_3$: 210.1287 (M$^+$-Cl)

Found: 200.1282.

Reference Example 2

Production of 1-methoxycarbonyl-3-methyl-2-oxo-butyl-ammonium; chloride

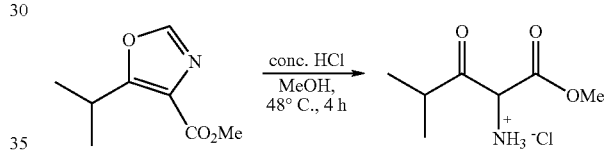

In a similar manner as Reference Example 1, an aimed compound was obtained from the corresponding oxazole. (Yield: 79%)

IR (KBr) 2979, 2642, 1751, 1720, 1508, 1438, 1387, 1275, 1234, 1013 cm$^{-1}$;

$^1$H-NMR (400 MHz, CD$_3$OD) δ 1.12 (d, J=6.4 Hz, 3H, (CH$_3$)$_2$CH), 1.24 (d, J=7.2 Hz, 3H, (CH$_3$)$_2$CH), 3.19-3.28 (sep, J=7.2 Hz, 1H, (CH$_3$)$_2$CH), 3.92 (s, 3H, CO$_2$CH$_3$);

$^{13}$C-NMR (100 MHz, CD$_3$OD) δ 17.7, 19.1, 39.8, 54.6, 165.3, 203.6;

HRMS (FAB, NBA) Calcd. for C$_7$H$_{14}$NO$_3$: 160.0974 (M$^+$-Cl).

Found: 160.0973.

Reference Example 3

Production of 3-butoxycarbonylaminoacetic acid benzyl ester

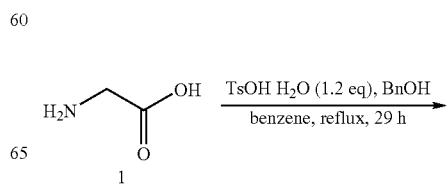

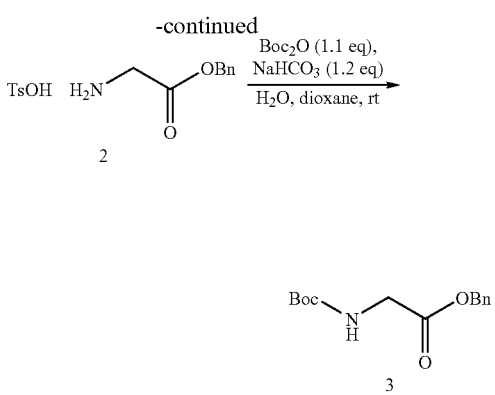

Benzene (469 mL) solution of glycine (35.0 g), BnOH (benzyl alcohol) (231 mL), TsOH.H₂O (p-toluenesulfonic acid monohydrate) (106 g, 1.2 equivalent) was refluxed with heating for 29 hours under azeotropic dehydration condition. Then, the reaction solution was cooled to room temperature, and the solid was filtered, and washed with diethylether to obtain aimed product 2 (168 g). This solid was used in the subsequent step without purification. The intermediate 2 (168 g) was dissolved in dioxane-water, sodium hydrogen carbonate (47 g, 1.2 equivalent) and BocO (di-t-butyl dicarbonate) (112 g, 1.1 equivalent) were added thereto, stirred for 3 hours and concentrated. The residue was washed with 1 mol/L sodium hydrogen sulfate aqueous solution and extracted 3 times with ethyl acetate. The organic phase was washed with saturated sodium hydrogen carbonate aqueous solution, dried over anhydrous sodium sulfate, and then filtered and concentrated. The residue was crystallized from diethylether-hexane to obtain aimed product 3 (first time 54.3 g, second time 51.2 g, third time 7.9 g; total 113.4 g, 427 mmol, 92%).

$^1$H-NMR (400 MHz, CDCl$_3$) δ 1.45 (s, 9H, (CH$_3$)$_3$C), 3.96 (d, J=5.7 Hz, 2H, CH$_2$NH), 5.00 (br, 1H, CH$_2$NH), 5.18 (s, 2H, CH$_2$Ph), 7.34-7.38 (m, 5H, Ar—H).

Reference Example 4

Production of 4a

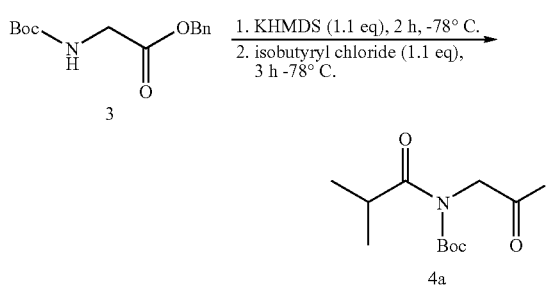

Starting material 3 (1.06 g, 4.00 mmol) was dissolved in tetrahydrofuran and cooled to −78° C. Then, KHMDS (potassium hexamethyl disilazide) (0.5 M solution 9.0 mL, 1.1 equivalent) was added over 10 minutes, and thereafter stirred at the same temperature for 2 hours. Further, isobutyryl chloride (0.46 mL, 1.1 equivalent) was added, and stirred at the same temperature for 3 hours. Then, the reaction solution was quenched with saturated ammonium chloride, and extracted 3 times with ethyl acetate-hexane (5:1). The resulting organic phase was washed with saturated sodium hydrogen carbonate aqueous solution, dried over anhydrous sodium sulfate, filtrated and concentrated. The residue was purified with silica gel chromatography (hexane:ethyl acetate=3:1) to obtain aimed product 4a (1.26 g, 94%).

IR (neat) 2978, 1747, 1698, 1457, 1370, 1216, 1148, 1028 cm$^{-1}$;

$^1$H-NMR (400 MHz, CDCl$_3$) δ 1.17 (d, J=6.8 Hz, 6H, (CH$_3$)$_2$CH), 1.44 (s, 9H, (CH$_3$)$_3$C), 3.72-3.76 (m, 1H, (CH$_3$)$_2$CH), 4.48 (s, 2H, CH$_2$N), 5.16 (s, 2H, CH$_2$Ph), 7.32-7.36 (m, 5H, Ar—H);

$^{13}$C-NMR (100 MHz, CDCl$_3$) δ 19.6, 27.8, 34.6, 45.6, 66.9, 83.7, 128.4, 128.5, 135.4, 152.1, 168.9, 180.2;

HRMS (FAB, NBA) Calcd. for C$_{18}$H$_{26}$NO$_5$: 336.1811 (M$^+$+1).

Found: 336.1811.

Reference Examples 5-9

Production of 4b-4f 4b-4f were produced in a similar manner as the process of Reference Example 4.

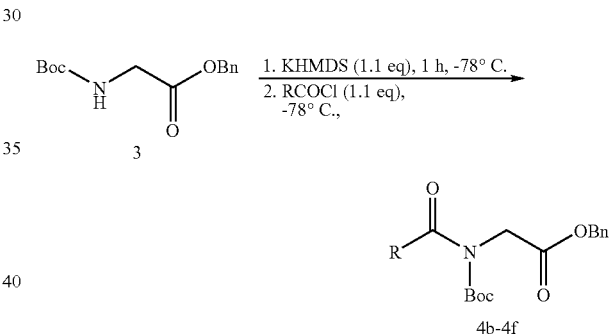

TABLE 1

| Reference Example No. | R | Reaction time (hr) | Product | Yield (%) |
|---|---|---|---|---|
| 5 | n-propyl | 3 | 4b | 88 |
| 6 | t-butyl | 12 | 4c | 93 |
| 7 | c-pentyl | 2 | 4d | 71 |
| 8 | c-hexyl | 12 | 4e | 94 |
| 9 | c-heptyl | 2 | 4f | 97 |

4b Colorless Oily Product

IR (Neat) 2969, 1747, 1456, 1370, 1216, 1149, 1031 cm$^{-1}$;

$^1$H-NMR (400 MHz, CDCl$_3$) δ 0.96 (d, J=7.3 Hz, 3H, CH$_3$CH$_2$ CH$_2$CO), 1.43 (s, 9H, (CH$_3$)$_3$C), 1.65-1.70 (m, 2H, CH$_3$CH$_2$ CH$_2$CO), 2.91 (d, J=7.3 Hz, 2H, CH$_3$CH$_2$ CH$_2$CO), 4.50 (s, 2H, CH$_2$N), 5.17 (s, 2H, CH$_2$Ph), 7.32-7.36 (m, 5H, Ar—H);

$^{13}$C-NMR (100 MHz, CDCl$_3$) δ 13.7, 18.4, 27.8, 39.8, 45.3, 66.9, 83.7, 128.4, 128.4, 128.6, 135.4, 152.2, 169.0, 175.6;

HRMS (FAB, NBA) Calcd. for $C_{18}H_{26}NO_5$: 336.1811 ($M^++1$).
Found: 336.1804.

4c Colorless Oily Product

IR (neat) 2974, 1747, 1694, 1456, 1336, 1148, 1010 $cm^{-1}$;
$^1$H-NMR (400 MHz, $CDCl_3$) δ 1.35 (s, 9H, $(CH_3)_3CCON$), 1.44 (s, 9H, $(CH_3)_3COCO$), 4.33 (s, 2H, $CH_2N$), 5.16 (s, 2H, $CH_2Ph$), 7.33-7.36 (m, 5H, Ar—H);
$^{13}$C-NMR (100 MHz, $CDCl_3$) δ 27.1, 27.8, 27.9, 43.1, 48.3, 66.0, 66.9, 83.2, 127.6, 127.9, 128.3, 128.3, 128.4, 128.5, 135.4, 152.7, 169.1, 184.6;
HRMS (FAB, NBA) Calcd. for $C_{19}H_{28}NO_5$: 350.1967 ($M^++1$).
Found: 350.1976.

4d

IR (KBr) 2971, 2871, 1746, 1695, 1455, 1370, 1148, 1048, 1027 $cm^{-1}$;
$^1$H-NMR (400 MHz, $CDCl_3$) δ 1.43 (s, 9H, $(CH_3)_3COCO$), 1.53-1.94 (m, 8H, c-Pen-$CH_2$) 3.80-3.85 (m, 1H, c-Pen-CH), 4.49 (s, 2H, $CH_2N$), 5.16 (s, 2H, $CH_2Ph$), 7.31-7.37 (m, 5H, Ar—H);
$^{13}$C-NMR (100 MHz, $CDCl_3$) δ 25.9, 27.8, 30.4, 45.2, 45.7, 66.9, 83.5, 128.5, 135.4, 152.1, 169.0, 179.1;
HRMS (FAB, NBA) Calcd. for $C_{20}H_{28}NO_5$: 362.1967 ($M^++1$).
Found: 362.1932.

4e White Solid

IR (KBr) 2931, 2853, 1737, 1691, 1450, 1368, 1323, 1193, 1146 $cm^{-1}$;
$^1$H-NMR (400 MHz, $CDCl_3$) δ 1.21-1.42 (m, 4H, c-Hex-$CH_2$), 1.67-1.80 (m, 4H, c-Hex-$CH_2$), 1.91-2.05 (m, 2H, c-Hex-$CH_2$), 3.46 (tt, J=3.3, 11.2 Hz, CHCON), 4.47 (s, 2H, $CH_2N$), 5.15 (s, 2H, $CH_2Ph$), 7.32-7.36 (m, 5H, Ar—H);
$^{13}$C-NMR (100 MHz, $CDCl_3$) δ 25.7, 25.9, 27.8, 29.7, 44.4, 45.7, 66.9, 83.6, 128.4, 128.5, 135.4, 152.1, 169.0, 179.1;
HRMS (FAB, NBA) Calcd. for $C_{21}H_{30}NO_5$: 376.2124 ($M^++1$).
Found: 376.2148.

4f White Solid

IR (neat) 2929, 2857, 1741, 1698, 1457, 1339, 1149, 1043 $cm^{-1}$;
$^1$H-NMR (400 MHz, $CDCl_3$) δ 1.44-1.66 (m, 17H, c-Hep-H, $(CH_3)_3C$), 1.72-1.78 (m, 2H, c-Hep-H), 1.90-1.97 (m, 2H, c-Hep-H), 3.64-3.71 (m, 1H, CHCON), 4.47 (s, 2H, $CH_2CO_2CH_2Ph$), 5.16 (s, 2H, $CH_2CO_2CH_2Ph$), 7.30-7.38 (m, 5H, Ar—H);
$^{13}$C-NMR (100 MHz, $CDCl_3$) δ 26.5, 27.8, 31.6, 45.2, 45.6, 66.9, 83.5, 128.5, 135.4, 152.1, 169.0, 180.1;
HRMS (FAB, NBA) Calcd. for $C_{22}H_{32}NO_5$: 390.2280 ($M^++1$).
Found: 390.2266.

Reference Example 10

Production of 5a

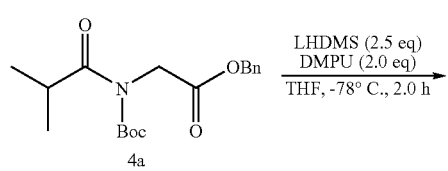

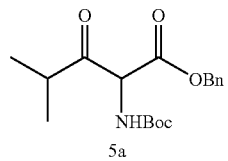

A THF (tetrahydrofuran) solution of 4a was cooled to −78° C. In the resulting solution, DMPU (1,1-dimethyl-3,4,5,6-tetrahydro-2-pyrimidinone) (2.0 equivalents) and LHMDS (lithium hexamethyidisilazide) (2.5 equivalents) were added over 10 minutes, and thereafter stirred at the same temperature for 2 hours. Then, the reaction solution was quenched with saturated ammonium chloride, and extracted 3 times with ethyl acetate-hexane (5:1). The resulting organic phase was washed with saturated sodium hydrogen carbonate water, dried over anhydrous sodium sulfate, filtrated and concentrated. The residue was purified with silica gel chromatography to obtain aimed product 5a (yield: 85%).

IR (neat) 3431, 2977, 1759, 1715, 1496, 1367, 1251, 1162 $cm^{-1}$;
$^1$H-NMR (400 MHz, $CDCl_3$) δ 0.99 (d, J=6.8 Hz, 3H, $(CH_3)_2CH$), 1.14 (d, J=7.1 Hz, 3H, $(CH_3)_2CH$), 1.44 (s, 9H, $(CH_3)_3C$), 2.94-2.99 (m, 1H, $(CH_3)_3CH$), 5.15-5.29 (m, 3H, CHNH, $CH_2Ph$), 5.73 (d, J=7.0 Hz, 1H, CHNH), 7.31-7.38 (m, 5H, Ar—H);
$^{13}$C-NMR (100 MHz, $CDCl_3$) δ 17.4, 18.7, 28.2, 38.4, 62.1, 68.0, 80.5, 128.4, 128.6, 134.7, 154.8, 166.7, 205.1;
HRMS (FAB, NBA) Calcd. for $C_{18}H_{26}NO_5$: 336.1811 ($M^++1$).
Found: 336.1816.

Reference Examples 11-15

Production of 5b-5f 5b-5f were produced in a similar manner as the process of Reference Example 10.

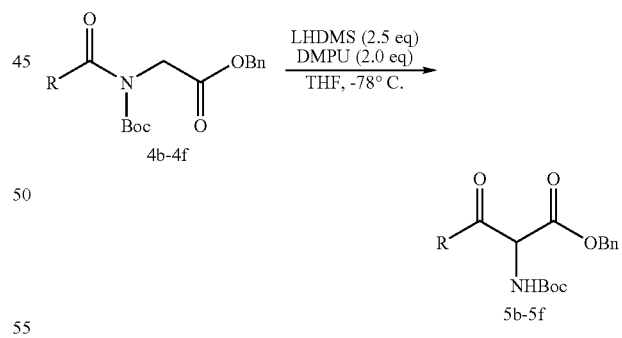

TABLE 2

| Reference Example No. | R | Reaction time (hr) | Product | Yield (%) |
|---|---|---|---|---|
| 11 | n-propyl | 1.5 | 5b | 87 |
| 12 | t-butyl | 2 | 5c | 75 |
| 13 | c-pentyl | 2 | 5d | 90 |
| 14 | c-hexyl | 6 | 5e | 84 |
| 15 | c-heptyl | 2 | 5f | 99 |

5b Colorless Oily Product

IR (neat) 3432, 2970, 1759, 1715, 1496, 1368, 1253, 1163 cm$^{-1}$;

$^1$NMR (400 MHz, CDCl$_3$) δ 0.83 (t, J=7.3 Hz, 3H, CH$_3$CH$_2$CH$_2$CO), 1.44 (s, 9H, (CH$_3$)$_3$CO), 1.52-1.62 (m, 2H, CH$_3$CH$_2$CH$_2$CO), 2.52-2.60 (m, 2H, CH$_3$CH$_2$CH$_2$CO), 5.05 (d, J=7.1 Hz, 1H, CHNH), 5.16 (d, J=12.3 Hz, 1H, CH$_2$Ph), 5.29 (d, J=12.3 Hz, 1H, CH$_2$Ph), 5.74 (d, J=6.8 Hz, 1H, CHNH), 7.31-7.38 (m, 5H, Ar—H);

$^{13}$C-NMR (100 MHz, CDCl$_3$) δ 13.4, 16.8, 19.5, 27.8, 28.2, 42.4, 63.7, 68.0, 80.5, 128.4, 128.6, 134.7, 154.9, 166.6, 201.0;

HRMS (FAB, NBA) Calcd. for C$_{18}$H$_{26}$NO$_5$: 336.1811 (M$^+$+1).

Found: 336.1788.

5c

IR (neat) 3376, 2977, 1758, 1713, 1504, 1368, 1326, 1252, 1162 cm$^{-1}$; $^1$H-NMR (400 MHz, CDCl$_3$) δ 1.18 (s, 9H, (CH$_3$)$_3$CCOCH), 1.43 (s, 9H, (CH$_3$)$_3$COCO), 5.15 (d, J=12.3 Hz, 1H, CH$_2$Ph), 5.20 (d, J=12.3 Hz, 1H, CH$_2$Ph), 5.52 (m, 2H, COCHNH), 7.29-7.37 (m, 5H, Ar—H);

$^{13}$C-NMR (100 MHz, CDCl$_3$) δ 26.1, 28.2, 44.7, 57.0, 67.7, 80.6, 128.3, 128.5, 128.6, 154.8, 167.6, 208.0;

HRMS (FAB, NBA) Calcd. for C$_{19}$H$_{28}$NO$_5$: 350.1967 (M$^+$+1).

Found: 350.1913.

5d

IR (neat) 3430, 2967, 2871, 1759, 1714, 1489, 1367, 1254, 1162 cm$^{-1}$;

$^1$H-NMR (400 MHz, CDCl$_3$) δ 1.34-1.94 (m, 17H, c-Pen-CH$_2$, (CH$_3$)$_3$CO), 3.14-3.18 (m, 1H, CHCOCHNH), 5.13-5.17 (m, 2H, CHNH, CH$_2$Ph), 5.29 (d, J=12.0 Hz, 1H, CH$_2$Ph), 5.76 (d, J=6.8 Hz, 1H, CHNH), 7.35-7.38 (m, 5H, Ar—H);

$^{13}$C-NMR (100 MHz, CDCl$_3$) δ 26.0, 26.0, 28.2, 28.5, 30.3, 48.8, 63.5, 67.9, 80.5, 128.6, 134.8, 154.8, 166.8, 203.7;

HRMS (FAB, NBA) Calcd. for C$_{20}$H$_{28}$NO$_5$: 362.1967 (M$^+$+1).

Found: 362.1933.

5e

IR (neat) 3431, 2978, 2932, 2856, 1755, 1713, 1495, 1453, 1368, 1337, 1251, 1161 cm$^{-1}$;

$^1$H-NMR (400 MHz, CDCl$_3$) δ 1.05-1.92 (m, 19H, c-Hex-CH$_2$, (CH$_3$)$_3$CO), 2.64-2.68 (m, 1H, CHCOCHNH), 5.14 (d, J=12.1 Hz, 1H, CH$_2$Ph), 5.18 (d, J=7.1 Hz, 1H, CHNH), 5.31 (d, J=12.1 Hz, 1H, CH$_2$Ph), 5.73 (d, J=7.1 Hz, 1H, CHNH), 7.31-7.36 (m, 5H, Ar—H);

$^{13}$C-NMR (100 MHz, CDCl$_3$) δ 25.0, 25.5, 25.7, 27.6, 28.3, 29.1, 48.2, 62.3, 68.0, 80.5, 128.6, 128.7, 134.8, 154.9, 166.7, 204.0;

HRMS (FAB, NBA) Calcd. for C$_{21}$H$_{30}$NO$_5$: 376.2124 (M$^+$+1).

Found: 376.2118.

5f

IR (neat) 3429, 2978, 2928, 2856, 1754, 1713, 1492, 1367, 1338, 1254, 1163 cm$^{-1}$;

$^1$H-NMR (400 MHz, CDCl$_3$) δ 1.24-1.93 (m, 21 H, c-Hep-CH$_2$, (CH$_3$)$_3$C), 2.88 (s, 1H CHCOCHNH), 5.14 (d, 1H, J=12.0 Hz, CH$_2$Ph), 5.18 (d, 1H, J=7.6 Hz, CHCOCHNH), 5.30 (d, 1H, J=12.0 Hz, CH$_2$Ph), 5.73 (d, J=6.8 Hz, 1H, CHCOCHNH), 7.35-7.38 (m, 5H, Ar—H);

$^{13}$C-NMR (100 MHz, CDCl$_3$) δ 26.2, 26.5, 28.0, 28.1, 28.2, 29.1, 30.3, 49.4, 62.4, 67.9, 80.4, 128.5, 128.6, 134.8, 154.9, 166.7, 204.4;

HRMS (FAB, NBA) Calcd. for C$_{22}$H$_{32}$NO$_5$: 390.2280 (M$^+$+1).

Found: 390.2263.

Reference Example 16

Production of 6a

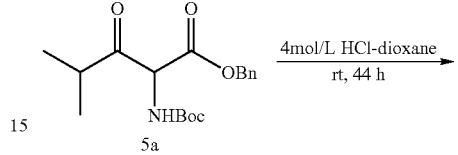

5a was dissolved in 4 mol/L hydrochloric acid-dioxane, stirred at room temperature for 44 hours, and then the reaction solution was concentrated. The residue was pulverized in diethyl ether, and aimed product 6a was filtered. The resulting solid was used in the subsequent step as such. (yield: 97%)

IR (KBr) 3403, 2972, 2936, 2654, 1762, 1736, 1523, 1267 cm$^{-1}$;

$^1$H-NMR (400 MHz, CDCl$_3$) δ 0.96 (d, J=6.4 Hz, 3H, (CH$_3$)$_2$CH), 1.22 (d, J=6.7 Hz, 3H (CH$_3$)$_2$CH), 3.03-3.09 (m, 1H, (CH$_3$)$_2$CH), 5.24 (d, J=11.6 Hz, 2H, CH$_2$Ph), 5.33 (d, J=12.0 Hz, 2H, CH$_2$Ph), 5.47 (s, 1H, COCHN), 7.32-7.38 (m, 5H, Ar—H), 9.00 (br);

$^{13}$C-NMR (100 MHz, CDCl$_3$) δ 17.1, 18.9, 38.9, 60.4, 67.0, 69.2, 128.6, 128.7, 128.8, 134.1, 163.3, 202.1;

HRMS (FAB, NBA) Calcd. for C$_{13}$H$_{18}$NO$_3$: 236.1287 (M$^+$-Cl).

Found: 236.1272.

Reference Examples 17-21

Production of 6b-6f 6b-6f were produced in a similar manner as the process of Reference Example 16.

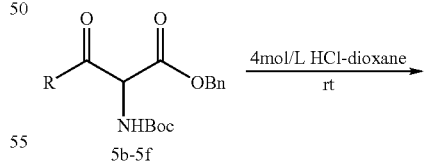

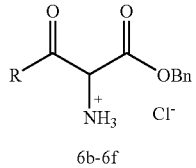

TABLE 3

| Reference Example No. | R | Reaction time (hr) | Product | Yield (%) |
|---|---|---|---|---|
| 17 | n-propyl | 48 | 6b | 80 |
| 18 | t-butyl | 62.5 | 6c | 91 |
| 19 | c-pentyl | 63 | 6d | quantitative |
| 20 | c-hexyl | 72 | 6e | quantitative |
| 21 | c-heptyl | 24 | 6f | quantitative |

6b

IR (KRr) 2968, 2935, 2599, 1750, 1725, 1459, 1280, 1226, 1147 cm$^{-1}$;

$^1$H-NMR (400 MHz, CD$_3$OD) δ 0.84 (t, J=7.6 Hz, 3H, CH$_3$CH$_2$CH$_2$CO), 1.50-1.62 (m, 2H, CH$_3$CH$_2$CH$_2$CO), 2.64-2.80 (m, 2H, CH$_3$CH$_2$CH$_2$CO), 5.32 (d, J=11.6 Hz, 1H, CH$_2$Ph), 5.41 (d, J=12.0 Hz, 1H, CH$_2$Ph), 7.36-7.46 (m, 5H, Ar—H);

$^{13}$C-NMR (100 MHz, CD$_3$OD) δ 13.6, 17.6, 43.4, 70.2, 129.8, 130.1, 135.8, 164.7, 199.2;

(FAB, NBA) Calcd. for C$_{13}$H$_{18}$NO$_5$: 236.1287 (M$^+$-Cl). Found: 236.1275.

6c

IR (KBr) 2971, 2900, 2867, 1747, 1718, 1543, 1508, 1265, 1239 cm$^{-1}$;

$^1$H-NMR (400 MHz, CDCl$_3$) δ 1.20 (s, 9H, (CH$_3$)$_3$C), 5.25 (s, 2H, CH$_2$Ph), 5.62 (s, 1H COCHN), 7.30-7.37 (m, 5H, Ar—H), 9.00 (br);

$^{13}$C-NMR (100 MHz, CDCl$_3$) δ 26.6, 44.9, 56.7, 69.2, 128.6, 128.7, 128.9, 134.0, 163.6, 204.4;

HRMS (FAB, NBA) Calcd. for C$_{14}$H$_{20}$NO$_3$: 250.1443 (M$^+$-Cl). Found: 250.1438.

6d

IR (KBr) 2951, 1746, 1720, 1508, 1458, 1269, 1207 cm$^{-1}$;

$^1$H-NMR (400 MHz, CDCl$_3$) δ 1.44-2.02 (m, 8H, c-Pen-H), 1.96-2.02 (m, 1H, c-Pen-H), 5.24 (d, J=12.0 Hz, 1H, CH$_2$Ph), 5.33-5.36 (m, 2H, CH$_2$Ph, COCHNH$_3$), 7.26-7.39 (m, 5H, Ar—H), 9.00 (br, COCHNH$_3$);

$^{13}$C-NMR (100 MHz, CDCl$_3$) δ 25.9, 26.0, 28.3, 30.6, 49.1, 61.6, 69.2, 128.6, 128.7, 34.2, 163.3, 200.7;

HRMS (FAB, NBA) Calcd. for C$_{15}$H$_{20}$NO$_3$: 262.1443 (M$^+$-Cl). Found: 262.1445.

6e

IR (KBr) 2931, 2854, 1747, 1719, 1509, 1266 cm$^{-1}$;

$^1$H-NMR (400 MHz, CDCl$_3$) δ 0.97-1.36 (m, 5H, c-Hex-H), 1.48-1.62 (m, 3H, c-Hex-H), 1.69-1.72 (m, 1H, c-Hex-H), 2.11-2.14 (m, 1H, c-Hex-H), 2.78 (tt, J=3.2, 11.6 Hz, 1H, c-Hex-H), 5.21 (d, J=12.0 Hz, 1H, CH$_2$Ph), 5.38 (d, J=12.0 Hz, 1H, CH$_2$Ph), 5.53 (s, 1H, COCHNH$_3$), 7.30-7.39 (m, 5H, Ar—H), 8.93 (br, COCHNH$_3$);

$^{13}$C-NMR (100 MHz, CDCl$_3$) δ 24.9, 25.5, 25.6, 27.2, 29.1, 48.3, 60.6, 69.2, 128.6, 128.8, 128.9, 134.2, 163.3, 200.8;

HRMS (FAB, NBA) Calcd. for C$_{16}$H$_{22}$NO$_3$: 276.1600 (M$^+$-Cl). Found: 276.1602.

6f

IR (KBr) 2927, 2624, 1746, 1720, 1509, 1459, 1281, 1198, 1119 cm$^{-1}$;

$^1$H-NMR (400 MHz, CDCl$_3$) δ 1.15-1.18 (m, 1H, c-Hep-H), 1.45-1.57 (m, 10H, c-Hep-H), 2.93-2.97 (m, 1H, c-Hep-H), 5.21 (d, 1H, J=12.0 Hz, 1H, CH$_2$Ph), 5.38 (d, J=13.2 Hz, 1H, CH$_2$Ph), 5.40 (s, 1H, COCHNH$_3$), 7.31-7.39 (m, 5H, Ar—H), 9.01 (br, COCHNH$_3$);

$^{13}$C-NMR (100 MHz, CDCl$_3$) δ 26.1, 26.5, 27.9, 28.1, 28.8, 30.3, 49.5, 60.7, 69.2, 128.6, 128.8, 128.9, 134.2, 163.3, 201.1;

HRMS (FAB, NBA) Calcd. for C$_{17}$H$_{24}$NO$_3$: 290.1756 (M$^+$-Cl). Found: 290.1765.

Reference Example 22

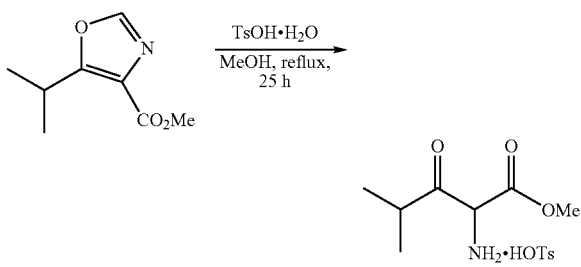

TsOH.H$_2$O (p-toluenesulfonic acid monohydrate) (230.0 mg) was added in methanol (3.0 mL) solution of oxazole (102.8 mg), and refluxed with heating for 25 hours. The resulting solution was concentrated and then pulverized in diethyl ether. The resulting crude product was used in the subsequent step without purification.

$^1$H-NMR (400 MHz, CDCl$_3$) δ 1.03 (d, J=6.8 Hz, 3H, (CH$_3$)$_3$CH), 1.11 (d, J=7.1 Hz, 3H, (CH$_3$)$_2$CH), 2.34 (s, 3H, Ar—CH$_3$), 3.06 (sep, J=7.0 Hz, 1H, (CH$_3$)$_3$CH), 5.36 (s, 1H, CHNH$_2$), 7.13 (d, J=8.1 Hz, 2H, Ar—H), 7.70 (d, J=8.2 Hz, 2H, Ar—H), 8.46 (s, 2H, CHNH$_2$).

Reference Example 23

Production of 6g

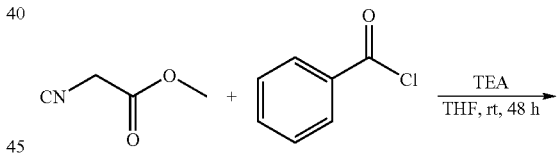

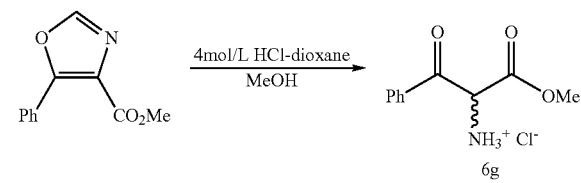

To THF (tetrahydrofuran) (50 mL), methylisocyanoate (2.97 g, 30 mmol), benzoyl chloride (2.97 g, 30 mmol) and TEA (triethyl amine) (12.6 mL, 90 mmol) were added, and stirred at room temperature for 48 hours. Then, the solvent was distilled off under reduced pressure, and ethyl acetate (100 ml) was added in the residue, and washed with water, 1 mol/L HCl (50 ml), saturated NaHCO$_3$ (50 ml) and saturated salt water (50 ml) in that order. After drying the solution over anhydrous sodium sulfate, precipitates were filtered off, and the solvent was distilled off under reduced pressure. The residue was purified with silica gel column chromatography (100 g, ethyl acetate:n-hexane=1:5) to obtain an oxazole compound (4.07 g, 20 mmol, 67%) as colorless solid.

$^1$H-NMR (400 MHz, CDCl$_3$) δ 3.96 (s, 3H), 7.45-7.53 (3H, m, Ar—H), 7.92 (s, 1H, oxazole-H), 8.00-8.12 (2H, m, Ar—H);

FT-IR $\nu_{max}$ (KBr): 3108, 1717, 1582, 1561, 1516, 1495, 1433, 1354, 1325, 1312, 1221, 1195, 1109, 1087, 1068, 1010, 936, 767, 688.

The oxazole compound (2.26 g, 11.1 mmol) was dissolved in 4 mol/L hydrochloric acid-dioxane (18 ml) and methanol (18 ml), and stirred at 60° C. for 24 hours. The resulting solution was cooled to room temperature, and then concentrated. The residue was dissolved in methanol, and concentrated again. This procedure was repeated 5 times to completely remove remaining hydrochloric acid, and then the resulting solid was washed with ether, and filtered. The resulting solid was recrystallized from ethyl acetate and methanol to obtain compound 6g (1.42 g, 6.2 mmol, 56%).

$^1$H-NMR (400 MHz, CD$_3$OD) δ 3.77 (s, 3H), 7.60 (t, J=7.6 Hz, 2H), 7.77 (tt, J=7.6 Hz, 1H), 8.17 (dd, J=1.6, 8.8 Hz, 2H);

$^{13}$C-NMR (100 MHz, CD$_3$OD) δ (ppm) 54.6, 130.1, 131.0, 134.9, 136.3, 165.4, 190.0;

FABMS (NBA) m/z: 194 (M-Cl$^-$)$^+$;

FT-IR $\nu_{max}$ (KBr): 3441, 2840, 1739, 1688, 1597, 1274, 1217, 684.

Reference Example 24

Production of 6h

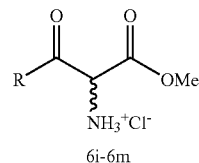

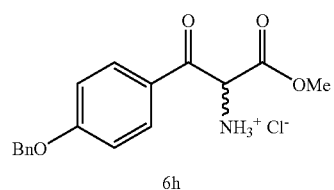

In a similar manner as Reference Example 23, aimed compound (6h) was obtained from the corresponding oxazole.

$^1$H-NMR (400 MHz, CD$_3$OD) δ 3.77 (s, 3H), 5.23 (s, 2H), 6.04 (s, 1H), 7.1-7.5 (m, 7H, Ar—H), 8.14 (d, J=7.2 Hz, 2H);

$^{13}$C-NMR (100 MHz, CD$_3$OD) δ (ppm) 54.5, 58.4, 71.5, 116.2, 127.8, 128.7, 129.3, 129.7, 133.6, 137.7, 165.8, 166.0, 187.9;

FABMS (NBA) m/z: 300 (M-Cl$^-$)$^+$;

FT-IR $\nu_{max}$ (KBr): 3445, 2969, 1759, 1685, 1603, 1509, 1276, 1254, 1222, 1176, 1075, 832, 743, 697.

Reference Examples 25-29

Production of 6i-6m

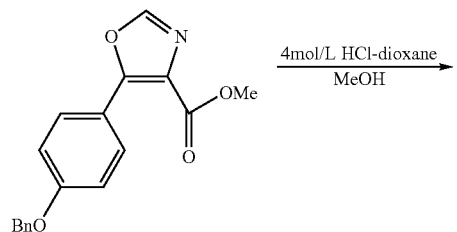

Compounds 6i-6m were produced by carrying out the similar process of Reference Example 23. In the meanwhile, the structure of each compound is as follows.

6i: R=p-methylphenyl group
6j: R=m-methylphenyl group
6k: R=β-naphthyl group
6l: R=2-furyl group
6m: R=p-bromophenyl group.

The results of instrumental analysis of each compound are as follows:

6i $^1$H-NMR (400 MHz, CD$_3$OD) δ 2.47 (s, 3H), 3.77 (s, 3H), 6.09 (s, 1H), 7.42 (2H, d, J=8.0 Hz), 8.05 (2H, d, J=8.0 Hz);

$^{13}$C-NMR (100 MHz, CD$_3$OD) δ (ppm) 21.8, 54.5, 58.7, 130.7, 131.2, 132.4, 148.0, 165.6, 189.3;

FT-IR $\nu_{max}$ (KBr): 2995, 2826, 2626, 1739, 1685, 1604, 1505, 1434, 1276, 1220, 1179, 1074, 968, 942, 863.

6j $^1$H-NMR (400 MHz, CD$_3$OD) δ 2.45 (s, 3H), 3.81 (s, 3H), 6.11 (s, 1H), 7.4-7.6 (2H, Ar—H), 7.9-8.0 (2H, Ar—H);

$^{13}$C-NMR (100 MHz, CD$_3$OD) δ (ppm) 21.3, 54.6, 58.8, 128.3, 130.0, 131.2, 135.0, 137.0, 140.3, 165.5, 190.1;

FT-IR $\nu_{max}$ (KBr): 3004, 2813, 2626, 1737, 1685, 1602, 1511, 1434, 1275, 1228, 1168, 1072, 948, 889, 866, 785, 685.

6k $^1$H-NMR (400 MHz, CD$_3$OD) δ 3.75 (s, 3H), 6.30 (s, 1H), 7.6-7.75 (2H, Ar—H), 7.9-8.15 (4H, Ar—H), 8.82 (1H, s, Ar—H);

$^{13}$C-NMR (100 MHz, CD$_3$OD) δ 54.6, 58.7, 125.0, 128.5, 129.0, 129.9, 131.0, 131.2, 132.2, 133.8, 134.3, 137.8, 165.6, 189.9;

FT-IR $\nu_{max}$ (KBr): 3440, 2819, 1739, 1688, 1622, 1594, 1502, 1434, 1280, 1236, 1174, 1008, 937, 811, 760.

6l $^1$H-NMR (400 MHz, CD$_3$OD) δ 3.82 (s, 3H), 5.78 (s, 1H), 6.80 (1H, dd, J=1.6, 4.0 Hz, Ar), 7.71 (1H, d, J=4.0 Hz, Ar—H), 8.0 (1H, d, J=1.6 Hz, Ar—H);

$^{13}$C-NMR (100 MHz, CD$_3$OD) δ 54.7, 58.4, 114.6, 124.1, 151.2, 151.3, 165.5, 177.1;

FT-IR $\nu_{max}$ (KBr): 3430, 2973, 2637, 1752, 1679, 1590, 1570, 1504, 1464, 1404, 1285, 1252, 1155, 1088, 1079, 1036, 1023, 991, 951, 910, 876, 841, 769.

6m $^1$H-NMR (400 MHz, CD$_3$OD) δ 3.78 (s, 3H), 6.11 (s, 1H), 7.79 (2H, Ar—H), 8.05 (2H, Ar—H);

$^{13}$C-NMR (100 MHz, CD$_3$OD) δ 547, 589, 131.5, 132.6, 133.4, 133.9, 165.2, 189.3;

FT-IR ν$_{max}$ (KBr): 2810, 1738, 1689, 1586, 1497, 1433, 1405, 1275, 1213, 1176, 1134, 1175, 966, 940, 864, 816, 764, 676.

Example 1

Production of β-hydroxy-α-aminocarboxylic acid derivative

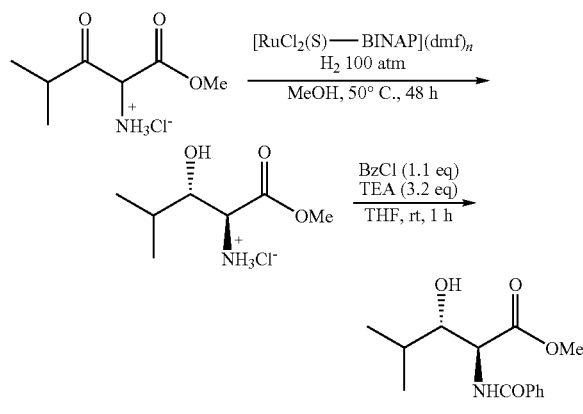

Under argon atmosphere, [RuCl$_2$(C$_6$H$_6$)]$_2$ (10.1 mg), (S)-BINAP (25.3 mg) and DMF (N,N-dimethylformamide) 400 μL were mixed in a Schlenk tube. The resulting solution was deaerated, and then stirred at 100° C. for 10 minutes. After lowering the temperature of the mixed solution to room temperature, the solution was dried under reduced pressure at 50° C. for 2.5 hours to obtain red-brown [RuCl$_2$ (S)-BINAP](dmf)$_n$ as a catalyst. 1-Methoxycarbonyl-3-methyl-2-oxo-butyl-ammonium; chloride (169.2 mg) produced in Reference Example 2 was dissolved in methanol (2.0 mL), deaerated and then the resulting solution was added in the above-mentioned catalyst through a cannula that the atmosphere therein was replaced with argon. The solution together with 1.0 ml of methanol used for washing was stirred under hydrogen (100 atm) at 50° C. for 48 hours. Then the reaction solution was concentrated to obtain an aimed product. The resulting crude product was subjected to benzoylation, and de and ee thereof were determined with instrumental analysis. In this example, de and ee were determined with $^1$H-NMR and HPLC, respectively.

Benzoylation

The resulting crude product was dissolved in THF (tetrahydrofuran) (1.7 mL). Next, BzCl (benzoyl chloride) (110 μL) and TEA (triethyl amine) (380 μL) were added therein at 0° C. After stirring at room temperature for 1 hour, water, ethyl acetate and hexane were added in the reaction solution to cease the reaction. Subsequently, the solution was separated into phases, and the resulting organic phase was washed with 1 mol/L hydrochloric acid solution and sodium hydrogen carbonate aqueous solution in that order, and dried over anhydrous sodium sulfonate, and then filtrated and concentrated. Subsequently, the resulting residue was fractionated and purified with silica gel chromatography (ethyl acetate:n-hexane=1:3) to obtain an aimed product (162.1 mg, 2-step 71%, 98% de, 56% ee).

HPLC analysis condition, column: CHIRALCEL OD-H (Daicel Chemical Industries, Ltd.), Mobile phase: n-hexane/i-propanol=85/15, Flow rate: 0.5 mL/min., Retention time: 2R, 3R form 10.6 min., 2S, 3S form 15.6 min.

[α]$_D^{25}$+35.4 (0.99, CHCl$_3$);

IR (neat) 3417, 2962, 1747, 1633, 1538, 1455, 1372, 1062, 1011 cm$^{-1}$;

$^1$H-NMR (400 MHz, CDCl$_3$) δ 1.02 (d, J=6.8 Hz, 3H, (CH$_3$)$_2$CH), 1.05 (d, J=6.6 Hz, 3H, (CH$_3$)$_2$CH), 1.77 (sep, J=6.6 Hz, 1H, (CH$_3$)$_2$CH), 2.91 (d, J=8.2 Hz, 1H, CHOH), 3.62 (dt, J=3.3, 8.6 Hz, 1H, CHOH), 3.82 (s, 3H, CO$_2$CH$_3$), 4.97 (dd, J=3.3, 7.3 Hz, 1H, CHNH) 7.14 (d, J=6.6 Hz, 1H, NH), 7.44-7.48 (m, 2H, Ar—H), 7.52-7.56 (m, 1H, Ar—H), 7.82-7.85 (m, 2H, Ar—H);

HRMS (FAB, NBA) Calcd. for C$_{14}$H$_{20}$NO$_4$: 266.1392 (M$^+$+1).

Found: 266.1408.

Example 2

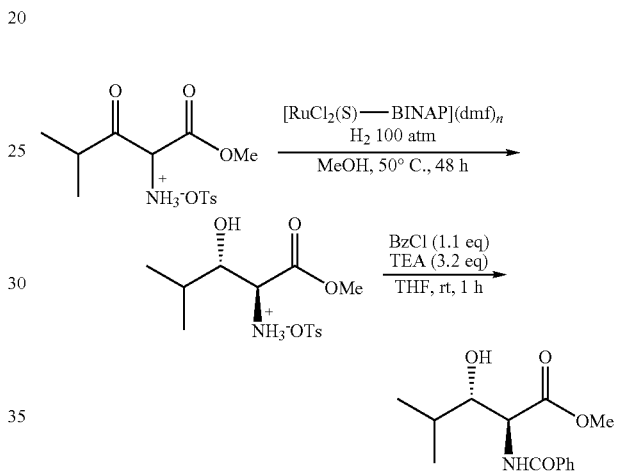

The procedures of Example 1 were repeated except that hydrochloride being starting material was changed to tosylate and the used amount of the catalyst was set to 6.7 mol % to obtain an aimed product. (Yield: 72% (total of 2-step), de: 94%, ee: 22%).

Examples 3-11

Effect of Solvents

The procedures of Example 1 were repeated except that the solvents were variously altered to obtain aimed products. In the meantime, the used amount of the catalyst was a range of 3.8 to 4.6 mol % based on that of the substrate. In addition, yield as shown in the total of 2-step.

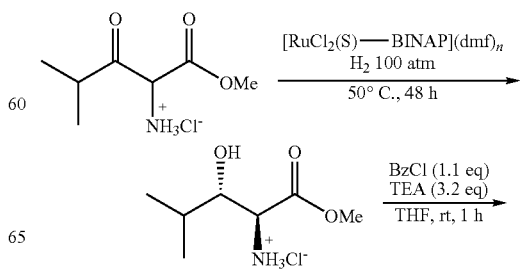

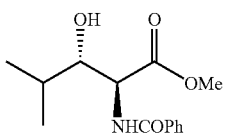

TABLE 4

| Example No. | Solvent | Yield (%) | de (%) | ee (%) |
| --- | --- | --- | --- | --- |
| 3 | methanol/CH$_2$Cl$_2$ | 80 | >99 | 70 |
| 4 | CH$_2$Cl$_2$ | 38 | 98 | 95 |
| 5 | n-propanol | 69 | 98 | 69 |
| 6 | n-propanol/CH$_2$Cl$_2$ | 92 | 98 | 82 |
| 7 | n-propanol/tetrahydrofuran | 91 | 95 | 81 |
| 8 | i-propanol | 81 | 98 | 81 |
| 9 | i-propanol/CH$_2$Cl$_2$ | 72 | 95 | 80 |
| 10 | 2-butanol | 91 | 91 | 74 |
| 11 | (CH$_2$OH)$_2$ | 84 | 91 | 57 |

Example 12

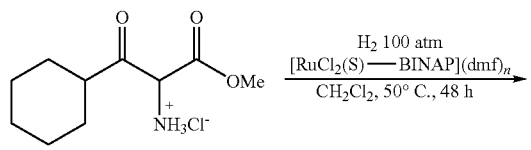

The procedures of Example 1 were repeated except that the substrate was changed to 2-cyclohexyl-1-methoxycarbonyl-2-oxo-ethyl-ammonium; chloride produced in Reference Example 1 and the solvent was changed to methylene chloride to obtain an aimed product (yield: 84% (total of 2-step), de: 95%. ee: 96%).

$[\alpha]_D^{26}$+35.5 (1.07, CHCl$_3$); melting point 94-97° C.

IR (KBr) 3545, 3493, 3281, 2927, 2854, 1739, 1630, 1542, 1363, 1230, 1209 cm$^{-1}$;

$^1$H-NMR (400 MHz, CDCl$_3$) δ 0.97-1.30 (m, 5H, c-Hex-H), 1.42-1.51 (m, 1H, c-Hex-H), 1.65-1.84 (m, 4H, c-Hex-H), 2.03-2.06 (m, 1H, c-Hex-H), 2.94 (d, J=8.4 Hz, 1H, CHOH), 3.68 (dt, J=3.2, 8.8 Hz, 1H, CHOH), 3.82 (s, 3H, CO$_2$CH$_3$), 4.97 (dd, J=3.2, 7.6 Hz, 1H, CHNH), 7.18 (d, J=7.2 Hz, NH), 7.44-7.47 (m, 2H, Ar—H), 7.51-7.56 (m, 1H, Ar—H), 7.82-7.84 (m, 2H, Ar—H);

HRMS (FAB, NBA) Calcd. for C$_{17}$H$_{24}$NO$_4$: 306.1705 (M$^+$+1).
Found: 306.1724.

HPLC analysis condition, column: CHIRALCEL OD-H (Daicel Chemical Industries, Ltd.), Mobile phase: n-hexane/i-propanol=85/15, Flow rate: 0.5 mL/min., Retention time: 2R, 3R form 11.2 min., 2S, 3S form 15.3 min.

Example 13

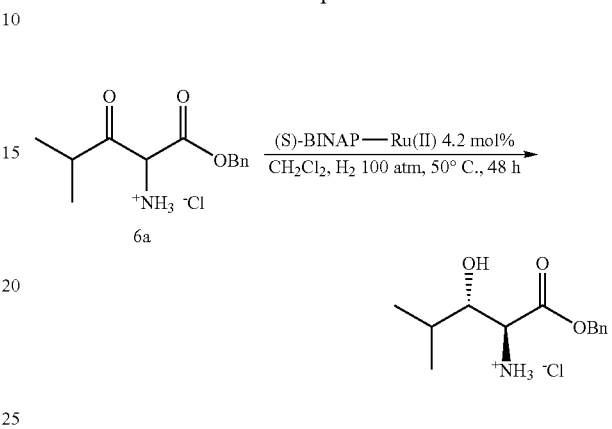

Under argon atmosphere, [RuCl$_2$(C$_6$H$_6$)]$_2$ (10.3 mg), (S)-BINAP (27.3 mg) and DMF (N,N-dimethylformamide) 400 μL were mixed in a Schlenk tube. The resulting solution was deaerated, and then stirred at 100° C. for 10 minutes. After lowering the temperature of the mixed solution to room temperature, the solution was dried under reduced pressure at 50° C. for 2.5 hours to obtain red-brown (S)-BINAP-Ru(II) as a catalyst. 6a (271.8 mg) was dissolved in methylene chloride (2.5 mL), deaerated and then the resulting solution was added in the above-mentioned catalyst through a cannula that the atmosphere therein was replaced with argon. The solution together with 1.0 ml of methanol used for washing was stirred under hydrogen (100 atm) at 50° C. for 48 hours. Then the reaction solution was concentrated to obtain an aimed product. The resulting crude product was subjected to benzoylation, and de and ee thereof were determined with instrumental analysis. In this example, de and ee were determined with $^1$H-NMR and HPLC, respectively.

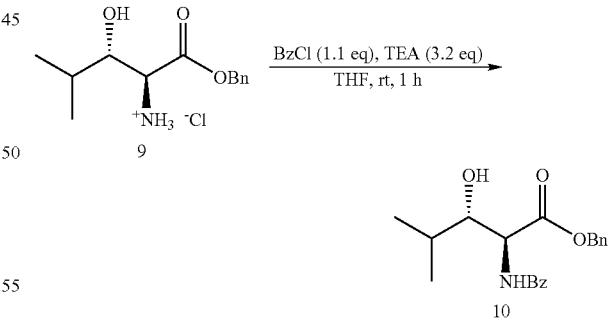

Benzoylation

The resulting crude product was dissolved in THF (tetrahydrofuran) (2.0 mL). Next, BzCl (benzoyl chloride) (130 μL) and TEA (triethyl amine) (440 μL) were added therein at 0° C. After stirring at room temperature for 1 hour, water, ethyl acetate and hexane were added in the reaction solution to cease the reaction. Subsequently, the solution was separated into phases, and the resulting organic phase was washed with 1 mol/L hydrochloric acid solution and sodium hydrogen carbonate aqueous solution in that order, and dried over anhydrous sodium sulfonate, and then filtrated and concentrated. Subsequently, the resulting residue was fractionated and purified with silica gel chromatography (ethyl acetate:n-hexane=1:2) to obtain an aimed product (yield: 87% (total of 2-step), de: >99%, ee: 96%).

HPLC analysis condition, column: CHIRALCEL OD-H (Daicel Chemical Industries, Ltd.), Mobile phase: n-hexane/i-propanol 90/10, Flow rate: 0.5 mL/min., Retention time: 2R, 3R form 21.6 min., 2S, 3S form 30.3 min.

$[\alpha]_D^{25}$ +33.9 (1.00, $CDCl_3$); melting point 95.5-96° C.

IR (KBr) 3414, 2961, 2935, 2858, 1749, 1647, 1519, 1192, 1064 $cm^{-1}$;

$^1$H-NMR (400 MHz, $CDCl_3$) δ 0.95 (d, J=6.6 Hz, 3H, $(CH_3)_2CH$), 1.13 (d, J=6.6 Hz, 3H, $(CH_3)_2CH$), 1.71 (d, 1H, $(CH_3)_2CH$), 2.92 (d, J=8.4 Hz, 1H, CHOH), 3.63 (dt, J=3.1, 8.4 Hz, 1H, CHOH), 4.99 (dd, J=3.3, 7.3 Hz, 1H, CHNH), 5.23 (d, J=12 Hz, 1H, $CH_2$-Ph), 5.29 (d, J=12 Hz, 1H, $CH_2$-Ph), 7.14 (d, J=7.3 Hz, 1H, CHNH), 7.34-7.39 (m, 5H, Ar—H), 7.43-7.47 (m, 2H, Ar—H), 7.52-7.56 (m, 1H, Ar—H), 7.81-7.83 (m, 2H, Ar—H);

$^{13}$C-NMR (100 MHz, $CDCl_3$) δ 18.9, 19.0, 31.5, 56.2, 67.6, 78.9, 127.2, 128.4, 128.6, 128.7, 132.0, 133.4, 134.9, 167.5, 170.8;

HRMS (FAB, NBA) Calcd. for $C_{20}H_{24}NO_4$: 342.1705 ($M^+$+1).

Found: 342.1682;

Elemental analysis, Calcd. for $C_{20}H_{24}NO_4$: C, 70.36; H, 6.79; N, 4.10.

Found: C, 70.26; H, 6.82; N, 4.06.

Examples 14-16

Effect of Solvents

The procedures of Example 13 were repeated except that the solvents were variously altered to obtain aimed products. Yield was shown in the total of 2-step.

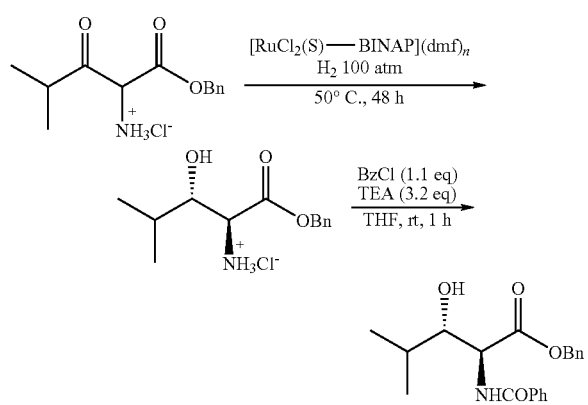

TABLE 5

| Example No. | Solvent | Catalyst (mol %) | Yield (%) | de (%) | ee (%) |
|---|---|---|---|---|---|
| 14 | n-propanol | 4.1 | 83 | 70 | 79 |
| 15 | i-propanol | 4.2 | 94 | 95 | 76 |
| 16 | monochlorobenzene | 6.2 | 85 | 67 | 86 |

Examples 17-20

Consideration of Reaction Time

The procedures of Example 13 were repeated except that the reaction time was altered to obtain aimed products. In the meantime, the used amount of the catalyst was a range of 3.9 to 4.1 mol % based on that of the substrate. In addition, yield was shown in the total of 2-step.

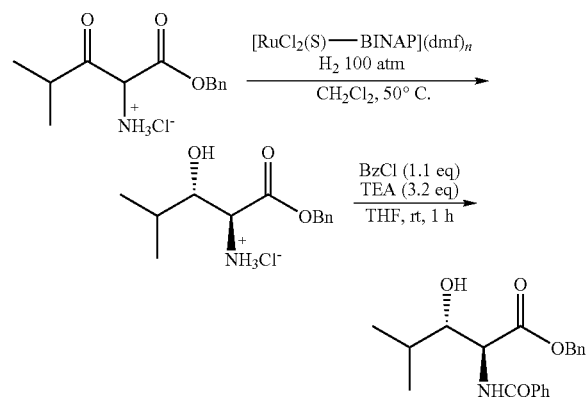

TABLE 6

| Example No. | Reaction Time | Yield (%) | de (%) | ee (%) |
|---|---|---|---|---|
| 17 | 24 | 88 | >99 | 92 |
| 18 | 13 | 81 | >99 | 98 |
| 19 | 6 | 84 | >99 | 98 |
| 20 | 3 | 55 | 89 | 98 |

Example 21

The procedures of Example 13 were repeated except that the solvent was changed to dichloroethane ($(CH_2Cl)_2$), the reaction temperature was changed to 100° C. and the reaction time was changed to 3 hours to obtain an aimed product. The yield was shown in the total of 2-step (yield: 90% (total of 2-step), de: 93%, ee: 92%).

Examples 22-32

The procedures of Example 13 were repeated except that the substrates and solvents were altered to obtain aimed products. Yield was shown in the total of 2-step.

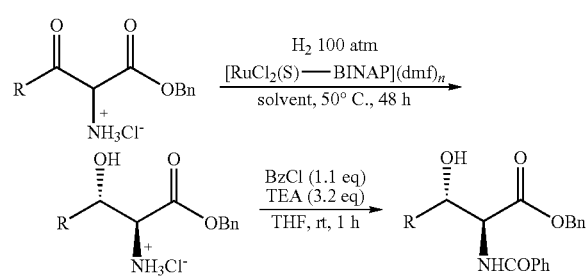

TABLE 7

| Example No. | R | Solvent | Yield (%) | de (%) | ee (%) |
|---|---|---|---|---|---|
| 22 | n-propyl | CH$_2$Cl$_2$ | 88 | 87 | 74 |
| 23 | n-propyl | CH$_2$Cl$_2$/n-propanol | 88 | 64 | 78 |
| 24 | n-propyl | n-propanol | 53 | 81 | 58 |
| 25 | t-butyl | n-propanol | 89 | 92 | 79 |
| 26 | c-pentyl | CH$_2$Cl$_2$ | 77 | 96 | 56 |
| 27 | c-pentyl | CH$_2$Cl$_2$/n-propanol | 82 | 97 | 94 |
| 28 | c-pentyl | n-propanol | 85 | 95 | 95 |
| 29 | c-hexyl | CH$_2$Cl$_2$ | 85 | 99 | 94 |
| 30 | c-hexyl | n-propanol | 80 | 96 | 54 |
| 31 | c-heptyl | CH$_2$Cl$_2$ | 94 | 94 | 79 |
| 32 | c-heptyl | n-propanol | 86 | 94 | 97 |

R=n-propyl $[\alpha]_D{}^{22}$+14.8 (1.01, CHCl$_3$); melting point 97.5-99° C.

IR (KBr) 3354, 2958, 2867, 1737, 1629, 1578, 1534, 1254, 1221 cm$^{-1}$;

$^1$H-NMR (400 MHz, CDCl$_3$) δ 0.85 (t, 3H, J=7.2 Hz, 3H, CH$_3$CH$_2$CH$_2$), 1.28-1.56 (m, 4H, CH$_3$CH$_2$CH$_2$), 3.29 (d, J=7.6 Hz, 1H, CHOH), 4.05-4.10 (m, 1H, CHOH), 4.93 (dd, J=3.2, 6.8 Hz, 1H, CHNH), 5.21 (d, J=12.4 Hz, 1H, CH$_2$Ph), 5.31 (d, J=12.4 Hz, 1H, CH$_2$Ph), 7.14 (d, J=6.8, 1H, CHNH), 7.26-7.56 (m, 8H, Ar—H), 7.82-7.84 (m, 2H, Ar—H);

$^{13}$C-NMR (100 MHz, CDCl$_3$) δ 13.8, 18.9, 35.3, 58.3, 67.7, 73.1, 127.2, 128.2, 128.4, 128.7, 132.1, 133.3, 134.9, 168.0, 170.3;

HRMS (FAB, NBA) Calcd. for C$_{20}$H$_{24}$NO$_4$: 342.1705 (M$^+$+1).

Found: 342.1699;

HPLC analysis condition, column: CHIRALCEL OD-H (Daicel Chemical Industries, Ltd.). Mobile phase: n-hexane/i-propanol 90/10, Flow rate: 0.5 mL/min., Retention time: 2R, 3R form 26.6 min., 2S, 3S form 32.3 min.

R=t-butyl $[\alpha]_D{}^{22}$+23.9 (1.01, CHCl$_3$);

IR (neat) 3373, 3064, 3033, 2958, 2908, 2872, 1731, 1644, 1538, 1487, 1177, 1078 cm$^{-1}$;

$^1$H-NMR (400 MHz, CDCl$_3$) δ 0.95 (s, 9H, (CH$_3$)$_3$C), 3.33 (d, J=10 Hz, 1H, CHOH), 3.6 (dd, J=3.2, 9.6 Hz, 1H, CHOH), 5.02 (dd, J=3.2, 7.6 Hz, 1H, CHNH), 5.20 (d, J=12.4 Hz, 1H, CH$_2$Ph), 5.24 (d, J=12.4 Hz, 1H, CH$_2$Ph), 7.10 (d, J=7.6, 1H, CHNH), 7.34-7.40 (m, 5H, Ar—H), 7.43-7.47 (m, 2H, Ar—H), 7.51-7.55 (m, 1H, Ar—H), 7.78-7.81 (m, 2H, Ar—H);

$^{13}$C-NMR (100 MHz, CDCl$_3$) δ 26.0, 35.4, 54.5, 67.6, 81.1, 127.1, 128.5, 128.6, 132.0, 133.4, 134.6, 167.3, 171.1;

HRMS (FAB, NBA) Calcd. for C$_{21}$H$_{26}$NO$_4$: 356.1862 (M$^+$+1).

Found: 356.1827;

HPLC analysis condition, column: CHIRALPAK AD (Daicel Chemical Industries, Ltd.), Mobile phase: n-hexane/i-propanol 90/10, Flow rate: 1.0 mL/min., Retention time: 2R, 3R form 26.8 min., 2S, 3S form 17.8 min.

R=cyclopentyl $[\alpha]_D{}^{24}$+20.5 (1.01, CHCl$_3$); melting point 109-111° C.

IR (KBr) 3414, 3342, 2938, 2867, 1746, 1644, 1521, 1488, 1195 cm$^{-1}$;

$^1$H-NMR (400 MHz, CDCl$_3$) δ 1.38-1.88 (m, 9H, c-Pen-H), 2.95 (d, J=8.0 Hz, 1H, CHOH), 3.78 (dt, J=2.88, 8.8 Hz, 1H, CHOH), 4.92 (dd, J=2.8, 7.2 Hz, 1H, CHNH), 5.21 (d, J=12.4 Hz, 1H, CH$_2$Ph), 5.31 (d, J=12.4 Hz, 1H, CH$_2$Ph), 7.19 (d, J=6.4, 1H CHNH), 7.34-7.39 (m, 5H, Ar—H), 7.43-7.47 (m, 2H, Ar—H), 7.51-7.56 (m, 1H, Ar—H), 7.81-7.84 (m, 2H, Ar—H);

$^{13}$C-NMR (100 MHz, CDCl$_3$) δ 25.1, 25.5, 29.0, 29.8, 43.5, 57.3, 67.5, 78.0, 127.2, 128.4, 128.6, 132.0, 133.4, 135.0, 167.6, 170.5;

HRMS (FAB, NBA) Calcd. for C$_{22}$H$_{26}$NO$_4$: 368.1862 (M$^+$+1).

Found: 368.1870;

HPLC analysis condition, column: CHIRALPAK AD (Daicel Chemical Industries, Ltd.), Mobile phase: n-hexane/i-propanol 90/10, Flow rate: 1.0 mL/min., Retention time: 2R, 3R form 25.2 min., 2S, 3S form 28.9 min.

R=cyclohexyl

Melting point 125-127° C.

IR (KBr) 3403, 2929, 2849, 1742, 1647, 1521, 1483, 1211 cm$^{-1}$;

$^1$H-NMR (400 MHz, CDCl$_3$) δ 0.95-1.78 (m, 10H, c-Hex-CH$_2$), 1.99 (d, J=12.1 Hz, 1H, CHC(OH)CHNH, 2.78 (d, J=8.8, 1 Hz, 1H, CHOH), 3.66 (dt, J=3.2 8.8 Hz, 1H, CHOH), 4.99 (dd, J=2.9, 7.3 Hz, 1H, CHNH), 5.18 (d, J=12.2 Hz, 1H, CH$_2$Ph), 5.34 (d, J=12.2 Hz, 1H, CH$_2$Ph), 7.17 (d, J=6.8, 1H, CHNH), 7.32-7.56 (m, 8H, Ar—H), 7.81-7.83 (m, 2H, Ar—H);

$^{13}$C-NMR (100 MHz, CDCl$_3$) δ 25.6, 26.1, 29.0, 29.2, 40.9, 55.7, 67.5, 77.9, 127.2, 128.5, 128.6, 131.9, 133.5, 135.0, 167.4, 170.8;

HRMS (FAB, NBA) Calcd. for C$_{23}$H$_{28}$NO$_4$: 382.2018 (M$^+$+1).

Found: 382.1933;

HPLC analysis condition, column: CHIRALPAK AD (Daicel Chemical Industries, Ltd.), Mobile phase: n-hexane/i-propanol 90/10, Flow rate: 1.0 mL/min., Retention time: 2R, 3R form 18.7 min., 2S, 3S form 32.3 min.

R=cycloheptyl $[\alpha]_D{}^{24}$+12.9 (1.01, CHCl$_3$);

IR (neat) 3418, 3064, 3033, 2925, 2854, 1734, 1646, 1539, 1190, 1082 cm$^{-1}$;

$^1$H-NMR (400 MHz, CDCl$_3$) δ 1.24-1.64 (m, 11H, c-Hep-H), 1.76-1.89 (m, 2H, c-Hep-H), 2.79 (dd, J=5.6, 8.4 Hz, 1H, CHOH), 3.70 (dt, J=3.2, 8.8 Hz, 1H, CHOH), 5.01 (dd, J=3.2, 7.2 Hz, 1H, CHNH), 5.18 (d, J=12.0 Hz, 1H, CH$_2$Ph), 5.32 (d, J=12.0 Hz, 1H, CH$_2$Ph), 7.13 (d, J=7.0, CHNH), 7.32-7.40 (m, 5H, Ar—H), 7.42-7.46 (m, 2H, Ar—H), 7.51-7.55 (m, 1H, Ar—H), 7.80-7.82 (m, 2H, Ar—H);

$^{13}$C-NMR (100 MHz, CDCl$_3$) δ 26.1, 26.2, 28.2, 28.9, 30.6, 42.3, 55.8, 67.5, 77.6, 127.2, 128.5, 128.6, 131.9, 133.5, 135.0, 167.4, 170.9;

HRMS (FAB, NBA) Calcd. for C$_{24}$H$_{30}$NO$_4$: 396.2175 (M$^+$+1).

Found: 396.2195;

HPLC analysis condition, column: CHIRALCEL OD-H (Daicel Chemical Industries, Ltd.), Mobile phase: n-hexane/i-propanol 90/10, Flow rate: 0.5 mL/min., Retention time: 2R, 3R form 30.5 min., 2S, 3S form 34.7 min.

Examples 33-43

Several reaction conditions were considered by changing the substrate to 2-cyclohexyl-1-methoxycarbonyl-2-oxo-ethyl-ammonium; chloride produced in Reference Example 1. Conversion rate means a value obtained by analyzing a reaction solution with HPLC and calculating the following equation in which concrete values of the areas of the substrate and product are substituted. In the meantime, 4.37 in the equation is a value used for correcting the sensitivity rate of the substrate and product in the measured wavelength.

Conversion Rate=Area of Product/(Area of Product+ Area of Substrate/4.37)×100

Analysis Condition

Analysis method: HPLC (Shimadzu LC10Avp), Reversed phase isoclatic analysis

Column: L-column ODS (Chemicals Evaluation and Research Institute, Japan) φ4.6 mm×250 mm+CAPCELL-PAKSCX UG80 (Shiseido Co., Ltd.) φ4.6 mm×250 mm.

Mobile phase: acetonitrile/100 mM KH$_2$PO$_4$ buffer=2/8 (v/v)
Flow rate: 1.0 ml/min.
Detection: UV215 nm
Retention time: Substrate 21.8 min., Product 23.4 min.
By analyzing benzoylated product with HPLC, ee was determined.

Analysis Condition of ee
Analysis method: HPLC (Shimadzu LC10Avp), Normal phase isoclatic analysis
Column: CHIRALCEL OD-H (Daicel Chemical Industries, Ltd.)
Mobile phase: n-hexane/i-propanol 85/15 (v/v)
Flow rate: 0.5 mL/min.
Detection: UV254 nm
Retention time: R form 11.2 min., S form 15.3 min.

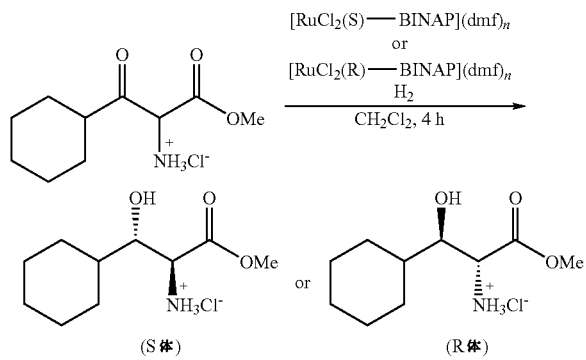

TABLE 8

| Example No. | Reaction Pressure (kgf·cm$^{-2}$) | Temperature (° C.) | Catalyst mol % | Config-uration | Conversion Rate (%) | ee (%) | Config-uration (R or S) |
|---|---|---|---|---|---|---|---|
| 33 | 30 | 50 | 4 | S | 95 | — | — |
| 34 | 30 | 50 | 4 | R | 98 | 95.3 | R |
| 35 | 20 | 50 | 4 | R | 95 | 96.8 | R |
| 36 | 10 | 50 | 4 | R | 90 | 97.1 | R |
| 37 | 30 | 90 | 5 | S | 99 | 95.1 | S |
| 38 | 30 | 70 | 5 | S | 98 | 95.2 | S |
| 39 | 30 | 50 | 5 | S | 97 | 96.4 | S |
| 40 | 30 | 50 | 5 | S | 98 | 96.7 | S |
| 41 | 30 | 50 | 0.5 | R | 92 | 94.8 | R |
| 42 | 30 | 50 | 0.1 | R | 90 | 82.6 | R |
| 43 | 30 | 50 | 0.01 | R | 84 | — | — |

Example 44
Production Process by Use of [Ir(cod)Cl]$_2$—(S)-MeO-Biphep-NaI as a Catalyst

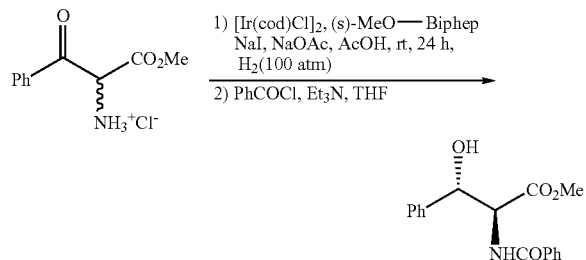

A solution obtained by adding [Ir(cod)Cl]$_2$ (2.5 mg, 0.0037 mmol), (S)-MeO-Biphep (5.8 mg, 0.01 mmol) and sodium iodide (2.3 mg, 0.015 mmol) in methylene chloride (1.0 mL) was deaerated by freeze-thaw method. The solution was stirred under argon atmosphere at room temperature for 10 minutes. The resulting yellow catalyst was dried under vacuum. To the catalyst, 6 g produced in Reference Example 23 (57.4 mg, 0.25 mmol), NaOAc (sodium acetate) (20.5 mg, 0.25 mmol) and deaerated AcOH (acetic acid) (1.2 mL) were added under argon atmosphere. The mixed solution was stirred at room temperature under hydrogen pressure of 100 atm. After stirring for 24 hours, the reaction solution was added in 1 mol/L hydrochoric acid (3.0 mL), and washed with 5 mL of diethyl ether. The resulting aqueous phase was concentrated and dried up at 40° C. under reduced pressure, and anhydrous ethanol was added to the resulting residue and pulverized. The white solid was filtered off, the resulting clear filtrate was concentrated under reduced pressure. The residue was dissolved in THF (tetrahydrofuran) (3 mL), and then PhCOCl (benzoyl chloride) (35.2 mg, 0.25 mmol) and Et$_3$N (triethyl amine) (75.9 mg, 0.75 mmol) were added therein at 0° C. After stirring at room temperature for 1 hour, water and ethyl acetate (10 mL) were added, and the resulting organic phase was washed with 1 mol/L hydrochloric acid (5 mL), saturated sodium hydrogen carbonate water (5 mL) and saturated salt water in that order, and dried over anhydrous sodium sulfonate, and precipitates were filtrated off and concentrated under reduced pressure. The residue was purified with silica gel column chromatography (20 g, ethyl acetate: n-hexane=1:2) to obtain an N-benzoyl form (57.8 mg, 0.19 mmol, 77%, >99% de, 89.6% ee) as colorless solid.

$^1$H-NMR (400 MHz, CDCl$_3$) δ 3.79 (3H, s), 4.56 (1H, d, J=5.6 Hz), 5.24 (1H, dd, J=3.6, 6.8 Hz), 5.40 (1H, dd, J=3.6, 5.6 Hz), 6.87 (1H, brd), 7.2-7.4 (5H, m, Ar—H), 7.4-7.5 (2H, m, Ar—H), 7.5-7.6 (1H, m, Ar—H), 7.7-7.8 (2H, m, Ar—H);

$^{13}$C-NMR (100 MHz, CDCl$_3$) δ (ppm) 52.6, 59.4, 75.1, 125.9, 127.1, 128.0, 128.3, 128.6, 132.1, 133.0, 139.1;

FT-IR ν$_{max}$ (KBr): 3338, 1744, 1644, 1525, 1229, 1173, 693.

FABMS (NBA) m/z: 300 (M+1);

HPLC analysis condition, column: CHIRALCEL OD-H (Daicel Chemical Industries, Ltd.), Mobile phase: n-hexane/i-propanol 85/15, Flow rate: 1.0 mL/min., Retention time: 2R, 3R form 8.6 min., 2S, 3S form 12.0 min.

Examples 45-49

The procedures of Example 44 were repeated except that the additive (iodine compound), acetic acid salt, temperature and reaction time were altered, to obtain aimed products. The yield was shown in the total of 2-step. In the meanwhile, the used amount of the catalyst was 3 mol % in the term of iridium based on that of the substrate, and the used amount of (S)-MeO-Biphep was 1.33 equivalent (4/3) based on that of iridium. In Table, the amount of iodine compound means equivalent number based on the used amount of iridium, the amount of acetic acid salt means equivalent number based on the used amount of the substrate, and TBAI means tetra n-butylammonium iodide.

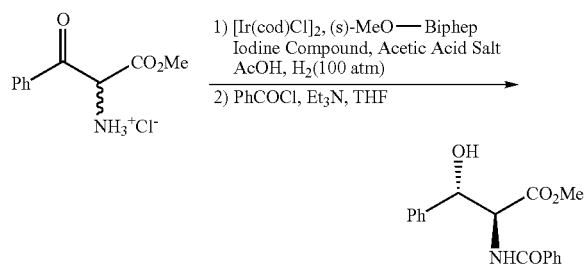

TABLE 10

| Example No. | R | Iodine Compound Kind* | Temperature (° C.) | Time (hr) | Yield (%) | de (%) | ee (%) |
|---|---|---|---|---|---|---|---|
| 49 | p-OBn-Ph | TBAI | r.t. | 48 | 51 | | 90 |
| 50 | p-Me-Ph | TBAI | r.t. | 48 | 64 | >99 | 86 |
| 51 | p-OBn-Ph | NaI | 30 | 96 | 64 | | 93 |
| 52 | p-Me-Ph | NaI | 30 | 96 | 76 | >99 | 94 |
| 53 | m-Me-Ph | NaI | 30 | 96 | 93 | >99 | 87 |
| 54 | β-Nap | NaI | 30 | 96 | 95 | 97 | 86 |
| 55 | p-Br-Ph | NaI | 30 | 96 | 87 | >99 | 75 |
| 56 | i-Pr | NaI | 30 | 96 | 50 | >99 | 82 |

Examples 57-74

Aimed products were produced by changing the ligand of Example 44 to (s)-BINAP and altering several conditions. The yield was shown in the total of 2-step. In the meanwhile, the used amount of the substrate:the used amount of iridium:

TABLE 9

| Example No. | Iodine Compound | | Acetic Acid Salt | | Temperature (° C.) | Time (hr) | Yield (%) | de (%) | ee (%) |
|---|---|---|---|---|---|---|---|---|---|
| | Kind | Amount | Kind* | Amount | | | | | |
| 45 | | 0 | AcONa | 1 | r.t | 3 | 79 | >99 | 77 |
| 46 | TBAI | 2 | AcONa | 1 | r.t | 24 | 77 | >99 | 87 |
| 47 | KI | 2 | AcOK | 1 | r.t | 24 | 57 | 96 | 87 |
| 48 | NaI | 2 | AcONa | 1 | 40 | 24 | 79 | 96 | 87 |
| 49 | TBAI | 1.1 | AcONa | I | r.t | 24 | 83 | >99 | 87 |

*AcONa and AcOK mean sodium acetate and potassium acetate, respectively.

Examples 49-56

The procedures of Example 44 were repeated except that the substrate, additive (iodine compound), temperature and reaction time were altered, to obtain aimed products. The yield was shown in the total of 2-step. In the meanwhile, the used amount of the substrate: the used amount of iridium:the used amount of (S)-MeO-Biphep:the amount of additive (iodine compound)=100:3:4:6, and the acetic acid salt (sodium acetate) was used in an amount of 1 equivalent based on the substrate. In Table, OBn is benzyloxy, Ph is phenyl, Me is methyl, Pr is propyl, β-Nap is naphthyl, and TBAI is tetra n-butylammonium iodide.

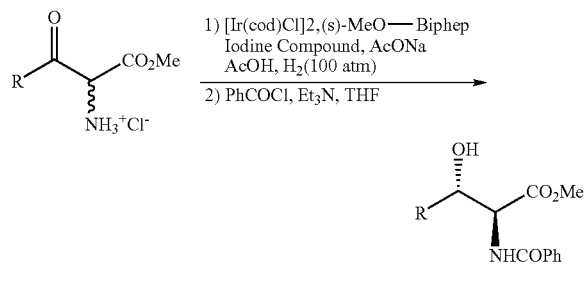

the used amount of (s)-BINAP=100:3:4. In Table, the amount of additive shows equivalent number based on the used amount of iridium, the amount of acetic acid salt shows equivalent number based on the substrate, and the abbreviations of solvent are as follows:

A: ethanol
B: n-propanol
C: i-propanol
D: methanol:benzene=1:2
E: n-propanol:tetrahydrofuran=1:2
F: i-propanol:acetic acid=1:1
G: tetrahydrofuran:acetic acid=1:1
H: acetic acid In addition, Phta means phthalimide, and TBAB and TBAI mean tetra n-butyl ammonium bromide and tetra n-butyl ammonium iodide.

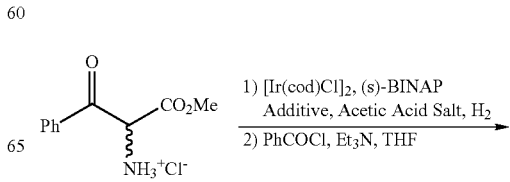

-continued

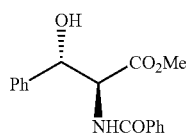

TABLE 11

| Example No. | Solvent | Additive Kind | Additive Amount | Acetic Acid Salt Kind* | Acetic Acid Salt Amount | Pressure atm | Time (hr) | Yield (%) | de (%) | ee (%) |
|---|---|---|---|---|---|---|---|---|---|---|
| 57 | A | | 0 | | 0 | 100 | 48 | 87 | 86 | 41 |
| 58 | B | | 0 | | 0 | 50 | 48 | 84 | 88 | 50 |
| 59 | C | | 0 | | 0 | 100 | 48 | 83 | 88 | 58 |
| 60 | D | | 0 | | 0 | 50 | 48 | 81 | | 40 |
| 61 | E | | 0 | | 0 | 100 | 48 | 37 | 92 | 66 |
| 62 | H | | 0 | AcONa | 1 | 100 | 48 | 83 | 98 | 69 |
| 63 | H | | 0 | AcONa | 1 | 100 | 48 | 79 | >99 | 69 |
| 64 | H | | 0 | AcONa | 1 | 100 | 3 | 90 | >99 | 69 |
| 65 | H | | 0 | AcOAm | 1.1 | 100 | 3 | 66 | 98 | 68 |
| 66 | H | | 0 | AcOLi | 1.1 | 100 | 3 | 58 | >99 | 69 |
| 67 | H | | 0 | AcONa | 3 | 100 | 3 | 79 | 96 | 68 |
| 68 | F | | 0 | AcONa | 1 | 100 | 48 | 58 | 86 | 57 |
| 69 | G | | 0 | AcONa | 1 | 100 | 48 | 57 | 97 | 54 |
| 70 | H | Phta | 2 | AcONa | 1 | 100 | 3 | 79 | >99 | 69 |
| 71 | H | TBAI | 2 | AcONa | 1 | 100 | 3 | 32 | >99 | 78 |
| 72 | H | TBAI | 2 | AcONa | 1 | 100 | 12 | 65 | >99 | 79 |
| 73 | H | TBAI | 2 | AcONa | 1 | 100 | 24 | 70 | >99 | 79 |
| 74 | H | TBAB | 2 | AcONa | 1 | 100 | 24 | 65 | >99 | 75 |

*AcONa, AcOAm and AcOLi mean sodium acetate, ammonium acetate and lithium acetate, respectively.

Example 75

The procedures of Example 64 were repeated except that the ligand was changed to (S)-T-BINAP, to obtain an aimed product. (Yield: 85% (total of 2-step), de: >99%, ee: 71%).

INDUSTRIAL APPLICABILITY

According to the present invention, anti forms of optically active β-hydroxy-α-aminocarboxylic acid derivatives that are useful as an intermediate for pharmaceuticals and agrochemicals can be efficiently produced.

The invention claimed is:

1. A process for producing optically active β-hydroxy-α-aminocarboxylic acid derivative of formula (2) or (3)

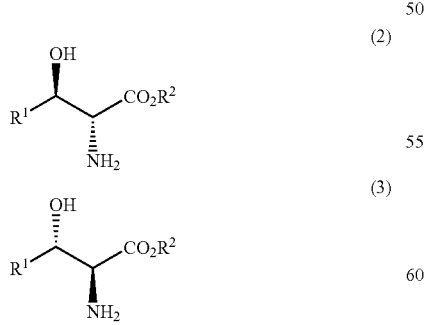

wherein $R^1$ is $C_{1-20}$ alkyl group which may be substituted either with $C_{4-12}$ aromatic group (the aromatic group may be substituted with halogen atom, $C_{1-6}$ alkyl group, $C_{1-6}$ alkoxy group, $C_{1-6}$ alkoxycarbonyl group, $C_{1-6}$ alkylcarbonyloxy group or $CONR^4R^5$ wherein $R^4$ and $R^5$ are independently of each other are hydrogen atom or $C_{1-6}$ alkyl group), $C_{1-6}$ alkoxy group, $C_{1-6}$ alkoxycarbonyl group or $CONR^4R^5$ wherein $R^4$ and $R^5$ are independently of each other are hydrogen atom or $C_{1-6}$ alkyl group, or $R^1$ is $C_{4-12}$ aromatic group which may be substituted either with halogen atom, $C_{1-6}$ alkyl group which may be substituted with $C_{4-12}$ aromatic group (the aromatic group may be substituted with halogen atom), $C_{1-6}$ alkoxy group which may be substituted with $C_{4-12}$ aromatic group (the aromatic group may be substituted with halogen atom), $C_{1-6}$ alkoxycarbonyl group which may be substituted with $C_{4-12}$ aromatic group (the aromatic group may be substituted with halogen atom), $C_{1-6}$ alkylcarbonyloxy group which may be substituted with $C_{4-12}$ aromatic group (the aromatic group may be substituted with halogen atom) or $CONR^4R^5$ wherein $R^4$ and $R^5$ are independently of each other are hydrogen atom or $C_{1-6}$ alkyl group, $R^2$ is $C_{1-20}$ alkyl group which may be substituted either with $C_{4-12}$ aromatic group (the aromatic group may be substituted with halogen atom, $C_{1-6}$ alkyl group, $C_{1-6}$ alkoxy group, $C_{1-6}$ alkoxycarbonyl group, $C_{1-6}$ alkylcarbonyloxy group or $CONR^4R^5$ wherein $R^4$ and $R^5$ are independently of each other are hydrogen atom or $C_{1-6}$ alkyl group), $C_{1-6}$ alkoxy group, $C_{1-6}$ alkoxycarbonyl group or $CONR^4R^5$ wherein $R^4$ and $R^5$ are independently of each other are hydrogen atom or $C_{1-6}$ alkyl group, or $R^2$ is $C_{4-12}$ aromatic group which may be substituted either with halogen atom, $C_{1-6}$ alkyl group, $C_{1-6}$ alkoxy group, $C_{1-6}$ alkoxycarbonyl group, $C_{1-6}$ alkylcarbonyloxy group or $CONR^4R^5$ wherein $R^4$ and $R^5$ are independently of each other are hydrogen atom or $C_{1-6}$ alkyl group, characterized by comprising subjecting an α-aminoacyl acetic acid ester compound of formula (1)

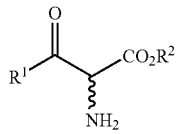
(1)

wherein $R^1$ and $R^2$ have the same meaning as the above, to hydrogenation by catalytic asymmetric hydrogenation in the presence of an acid,
wherein the catalyst used for the catalytic asymmetric hydrogenation is a complex of ruthenium or iridium having an optically active phosphine ligand.

2. The process for producing optically active β-hydroxy-α-aminocarboxylic acid derivative according to claim 1, wherein the optically active phosphine ligand is an optically active bidentate phosphine ligand.

3. The process for producing optically active β-hydroxy-α-aminocarboxylic acid derivative according to claim 2, wherein the Group VIII transition metal of the Periodic Table is ruthenium, and the optically active bidentate phosphine ligand is represented by formula (4)

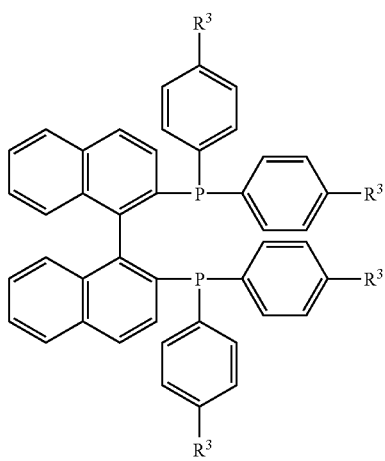
(4)

wherein $R^3$ is hydrogen atom, methyl group, or tertiary butyl group, absolute configuration is either S or R.

4. The process for producing optically active β-hydroxy-α-aminocarboxylic acid derivative according to claim 3, wherein the complex of a Group VIII transition metal of the Periodic Table is $RuHX^1(R^3\text{-BINAP})_2$, $RuX^2{}_2(R^3\text{-BINAP})$ or $Ru_2Cl_4(R^3\text{-BINAP})_2(Et_3N)$ wherein $R^3$-BINAP is the optically active bidentate phosphine ligand of formula (4), Et is ethyl group, $X^1$ and $X^2$ independently of each other are Cl, $ClO_4$, $BF_4$, $PF_6$, $OCOCH_3$, $OCOCF_3$, OCO-t-Bu or $OSO_2CF_3$, the complex may be further coordinated with N,N-dimethylformamide, benzene, $AlCl_3$, $SnCl_4$, $TiCl_4$ or $ZnCl_2$.

5. The process for producing optically active β-hydroxy-α-aminocarboxylic acid derivative according to claim 4, wherein the complex of a Group VIII transition metal of the Periodic Table is $RuX^2{}_2(R^3\text{-BINAP})$ wherein $X^2$ and $R^3$-BINAP have the same meaning as the above, the complex may be further coordinated with N,N-dimethylformamide, benzene, $AlCl_3$, $SnCl_4$, $TiCl_4$ or $ZnCl_2$.

6. The process for producing optically active β-hydroxy-α-aminocarboxylic acid derivative according to claim 5, wherein $RuX^2{}_2(R^3\text{-BINAP})$ further coordinated with N,N-dimethylformamide or benzene wherein $X^2$ is Cl, $R^3$-BINAP has the same meaning as the above is used.

7. The process for producing optically active β-hydroxy-α-aminocarboxylic acid derivative according to claim 2, wherein the Group VIII transition metal of the Periodic Table is iridium, and the optically active bidentate phosphine ligand is $R^3$-BINAP wherein $R^3$-BINAP has the same meaning as the above or a compound of formula (5)

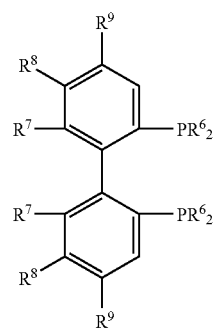
(5)

wherein $R^6$ is phenyl group, naphthyl group (the phenyl group and naphthyl group may be substituted with $C_{1-6}$ alkyl group or $C_{1-6}$ alkoxy group), cyclopentyl group or cyclohexyl group, $R^7$ is methyl group or methoxy group, $R^8$ is hydrogen atom, methyl group, methoxy group or chlorine atom, $R^9$ is hydrogen atom, methyl group, methoxy group, dimethylamino group or diethylamino group, absolute configuration is either S or R.

8. The process for producing optically active β-hydroxy-α-aminocarboxylic acid derivative according to claim 7, wherein an acetic acid salt is added in the reaction system.

9. The process for producing optically active β-hydroxy-α-aminocarboxylic acid derivative according to claim 8, wherein when the complex of a Group VIII transition metal of the Periodic Table is prepared, an iodine compound is added.

10. The process for producing optically active β-hydroxy-α-aminocarboxylic acid derivative according to claim 9, wherein the optically active bidentate phosphine ligand is a compound of the formula (5).

11. The process for producing optically active β-hydroxy-α-aminocarboxylic acid derivative according to claim 10, wherein when the complex of a Group VIII transition metal of the Periodic Table is prepared, $[Ir(cod)Cl]_2$ wherein cod is 1,5-cyclooctadiene is used.

12. The process for producing optically active β-hydroxy-α-aminocarboxylic acid derivative according to claim 1, wherein the acid is a strong acid.

* * * * *